(12) United States Patent
Sharratt et al.

(10) Patent No.: US 10,167,242 B2
(45) Date of Patent: Jan. 1, 2019

(54) PROCESS FOR PREPARING A C3-C7 (HYDRO) FLUOROALKENE BY DEHYDROHALOGENATION

(71) Applicant: MEXICHEM AMANCO HOLDING S.A. de C.V., Tlalnepantla (MX)

(72) Inventors: Andrew P Sharratt, Cheshire (GB); Claire E McGuinness, Cheshire (GB); Sheryl C Carolan, Cheshire (GB)

(73) Assignee: Mexichem Amanco Holding S.A. de C.V., Tlalnepantla (MX)

( * ) Notice: Subject to any disclaimer, the term of this patent is extended or adjusted under 35 U.S.C. 154(b) by 0 days.

(21) Appl. No.: 14/398,252

(22) PCT Filed: May 1, 2013

(86) PCT No.: PCT/GB2013/051129
§ 371 (c)(1),
(2) Date: Oct. 31, 2014

(87) PCT Pub. No.: WO2013/164618
PCT Pub. Date: Nov. 7, 2013

(65) Prior Publication Data
US 2015/0126786 A1 May 7, 2015

(30) Foreign Application Priority Data

May 2, 2012 (GB) .................................. 1207666.7

(51) Int. Cl.
*C07C 17/25* (2006.01)
*C07C 21/18* (2006.01)
(Continued)

(52) U.S. Cl.
CPC ............... *C07C 17/25* (2013.01); *B01J 21/04* (2013.01); *B01J 21/066* (2013.01); *B01J 23/04* (2013.01);
(Continued)

(58) Field of Classification Search
CPC ..................................................... C07C 17/25
See application file for complete search history.

(56) References Cited

U.S. PATENT DOCUMENTS

| | | |
|---|---|---|
| 1,868,869 A | 7/1930 | Barnitt |
| 2,015,593 A | 9/1935 | Derr |

(Continued)

FOREIGN PATENT DOCUMENTS

| | | |
|---|---|---|
| EP | 0169711 | 1/1986 |
| EP | 0366797 | 5/1990 |

(Continued)

OTHER PUBLICATIONS

Goodboy, K. P. et al "Production Processes, Properties, and Applications for Activated and Catalytic Aluminas" from Alumina Science and Technology Handbook Chemicals, 1990, pp. 93-98 (Year: 1990).*

(Continued)

*Primary Examiner* — Medhanit W Bahta
(74) *Attorney, Agent, or Firm* — Ryan Kromholz & Manion, S.C.

(57) ABSTRACT

The invention provides a process for preparing a $C_{3-7}$ (hydro)fluoroalkene comprising dehydrohalogenating a $C_{3-7}$ hydro(halo)fluoroalkane in the presence of a catalyst comprising a metal oxide supported on alumina, wherein the catalyst has a sodium content of less than about 800 ppm.

21 Claims, 7 Drawing Sheets

245fa conversion vs time

(51) Int. Cl.
  B01J 37/08    (2006.01)
  B01J 21/04    (2006.01)
  B01J 21/06    (2006.01)
  B01J 23/26    (2006.01)
  B01J 35/10    (2006.01)
  B01J 37/02    (2006.01)
  B01J 23/04    (2006.01)
(52) U.S. Cl.
  CPC ........... B01J 23/26 (2013.01); B01J 35/1019 (2013.01); B01J 37/0201 (2013.01); B01J 37/08 (2013.01)

(56) References Cited

U.S. PATENT DOCUMENTS

| | | | |
|---|---|---|---|
| 2,499,675 | A | 3/1950 | Owen |
| 3,201,199 | A | 8/1965 | Lindsay et al. |
| 3,223,483 | A * | 12/1965 | Osment ............... B01J 20/08 423/131 |
| 5,679,875 | A | 10/1997 | Aoyama et al. |
| 5,731,481 | A | 3/1998 | Cheminal et al. |
| 5,986,151 | A | 11/1999 | Van Der Puy |
| 6,124,510 | A * | 9/2000 | Elsheikh ............... C07C 17/25 570/156 |
| 2007/0037704 | A1 | 2/2007 | Rizkalla |
| 2008/0051611 | A1 | 2/2008 | Wang et al. |
| 2009/0099395 | A1 | 4/2009 | Sakyu et al. |
| 2009/0299107 | A1 | 12/2009 | Wang et al. |
| 2010/0022809 | A1 | 1/2010 | Cottrell et al. |
| 2010/0256426 | A1 | 10/2010 | Sakyu et al. |
| 2010/0305370 | A1 * | 12/2010 | Devic ............... B01J 23/866 570/156 |
| 2011/0015452 | A1 | 1/2011 | Devic et al. |
| 2011/0112338 | A1 * | 5/2011 | Smith ............... C07C 17/25 570/153 |
| 2011/0160498 | A1 | 6/2011 | Pigamo et al. |
| 2011/0178344 | A1 | 7/2011 | Nose et al. |
| 2011/0282112 | A1 | 11/2011 | Nappa et al. |
| 2012/0059200 | A1 | 3/2012 | Pokrovski et al. |
| 2012/0172639 | A1 | 7/2012 | Nappa et al. |

FOREIGN PATENT DOCUMENTS

| | | |
|---|---|---|
| EP | 0403108 | 12/1990 |
| EP | 0461297 | 12/1991 |
| EP | 0974571 | 1/2000 |
| EP | 1900716 | 3/2008 |
| EP | 1918269 | 5/2008 |
| EP | 2014637 | 1/2009 |
| EP | 2028172 | 2/2009 |
| EP | 2096096 | 9/2009 |
| EP | 2151425 | 2/2010 |
| EP | 2338866 | 6/2011 |
| EP | 2778150 | 9/2014 |
| FR | 2989374 | 10/2013 |
| JP | 11-140002 | 5/1999 |
| JP | 2009-091301 | 4/2009 |
| JP | 2009-097301 | 5/2009 |
| JP | WO 2011099604 A2 * | 8/2011 ............ C07C 17/25 |
| SU | 507551 | 3/1976 |
| WO | WO2005/037431 | 4/2005 |
| WO | WO2005/042451 | 5/2005 |
| WO | WO2007/079431 | 7/2007 |
| WO | WO2008/008350 | 1/2008 |
| WO | WO2008/0008350 | 1/2008 |
| WO | WO2008/030440 | 3/2008 |
| WO | WO2008/030443 | 3/2008 |
| WO | WO2008/040969 | 4/2008 |
| WO | WO2008/125825 | 10/2008 |
| WO | WO2009/015304 | 1/2009 |
| WO | WO2009/026082 | 2/2009 |
| WO | WO2010/021406 | 2/2010 |
| WO | WO2010/0141664 | 12/2010 |
| WO | WO2010/141664 | 12/2010 |
| WO | WO-2010141664 A1 * | 12/2010 ............ C07C 17/25 |
| WO | WO2012/006295 | 1/2012 |
| WO | WO2013/077189 | 5/2013 |
| WO | WO2014/003068 | 1/2014 |
| WO | WO2014/134821 | 9/2014 |

OTHER PUBLICATIONS

Briggs, W. S. "Pelleted Catalyst Systems" from Alumina Science and Technology Handbook Chemicals, 1990, pp. 289 (Year: 1990).*
Stiles, A. B. "Catalyst Supports and Supported Catalysts, Theoretical and Applied Concepts" 1987, pp. 11-55 (Year: 1987).*
International Preliminary Report on Patentability dated Nov. 13, 2014, regarding International Application No. PCT/GB2013/051129, 9 pages.
Kirk-Othmer Encyclopedia of Chemical Technology, 5th ed., "Aluminum Oxide (Alumina), Activated", vol. 2, 2004, pp. 391, 395-398.
G.J.K. Acres et al., "The Design and Preparation of Supported Catalysts", Catalysis, vol. 4, published Oct. 31, 2007, 30 pages.
Sumitomo Chemical Product Databook, p. 13, www.sumitomo-chem.co.jp, Retrieved on Dec. 14, 2015.
15710 Chemical Products, 2010, pp. 53-55.
Poisson et al., Alumina, Catalyst Supports and Supported Catalysts, Theoretical and Applied Concepts, Alvin B. Stiles, pp. 11-55; 1987.
Goodboy et al., Production Processes, Properties, and Applications for Activated and Catalytic Aluminas, Alumina Chemicals (Science and Technology Handbook), pp. 93-98, 1990.
Briggs, Pelleted Catalyst Systems, Alumina Chemicals, Science and Technology Handbook; p. 289; 1990.
Matar et al., Catalysis in Petrochemical Processes; Kluwer Academic Publishers; Netherlands; 1989; p. 118.

* cited by examiner

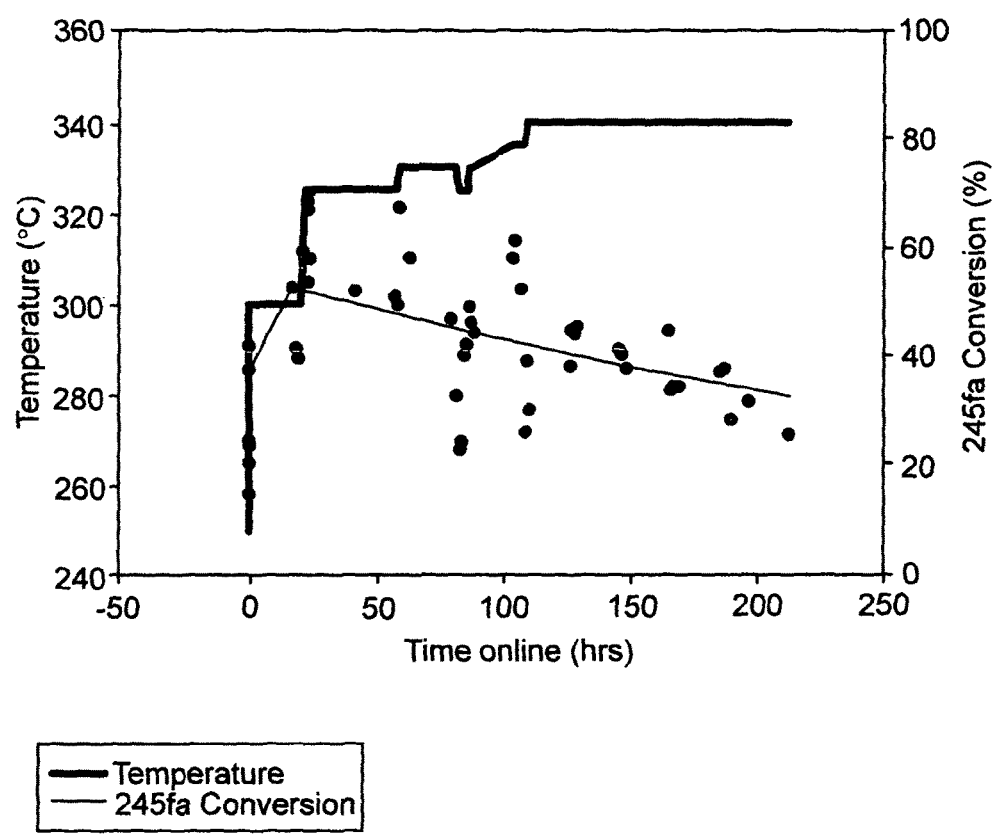
Figure 1: 245fa conversion vs time

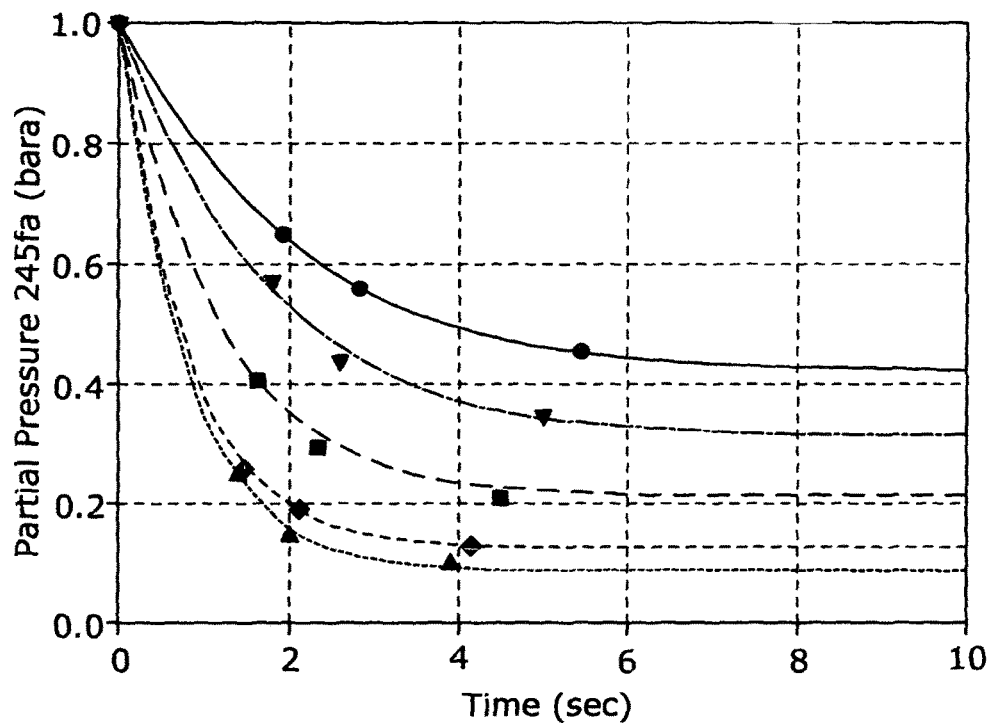
Figure 2: Data and fits to A=B+C Rate Law
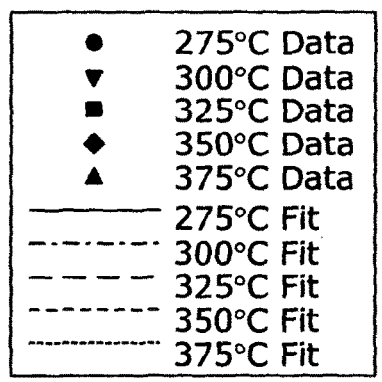

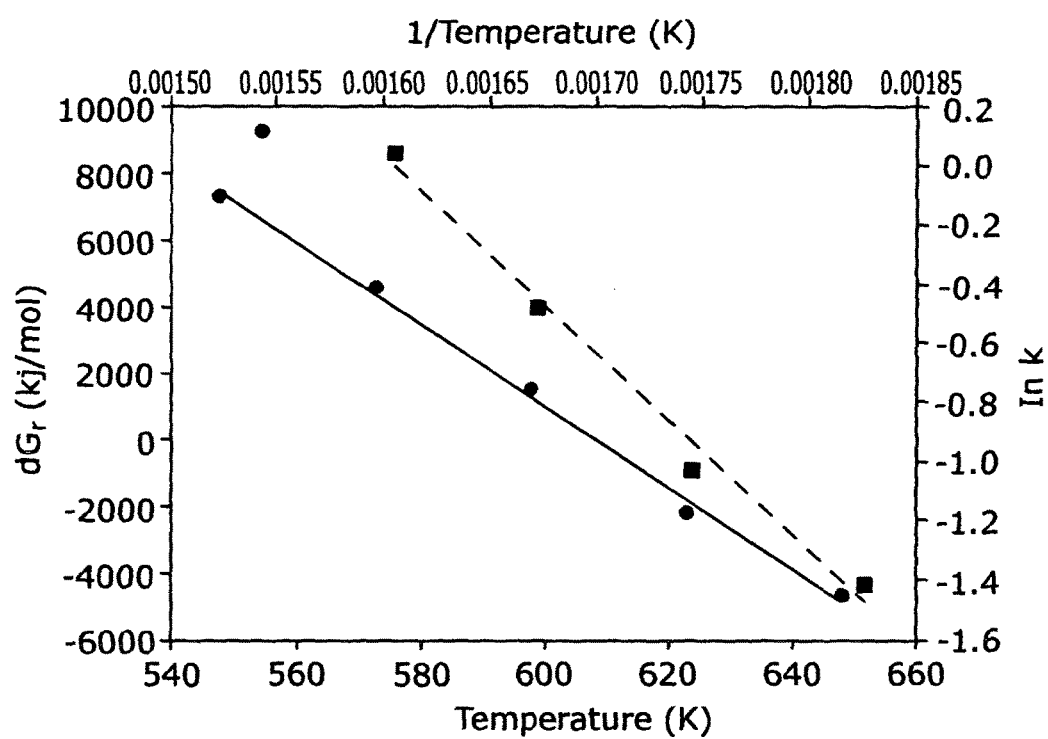
Figure 3: Gibbs and Arrhenius plot
- dGr vs T (K)
- ln k vs 1/T (K)

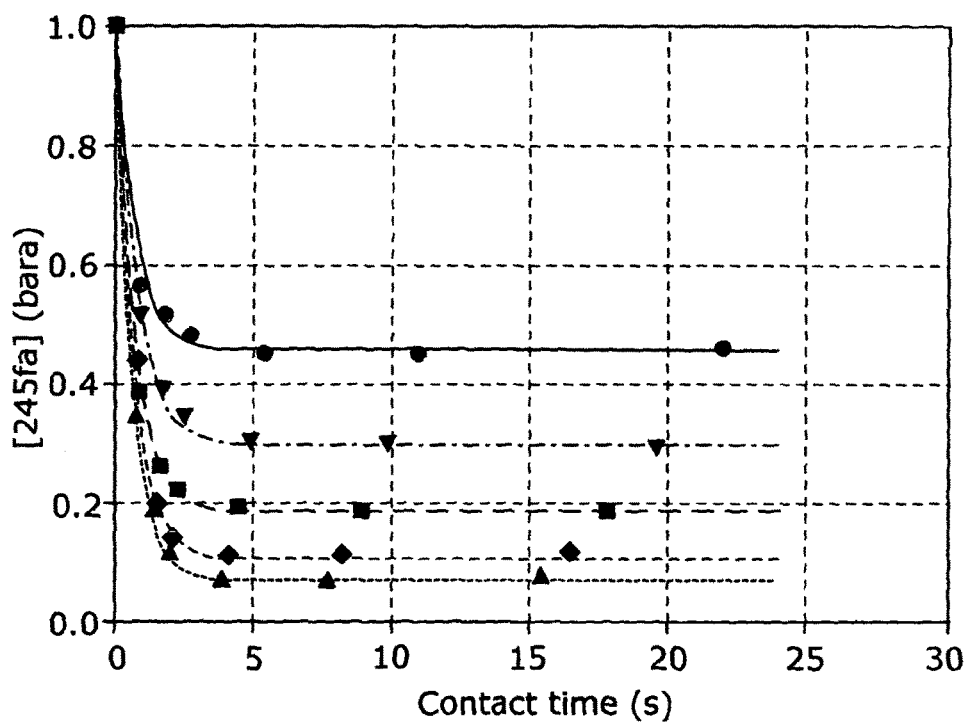
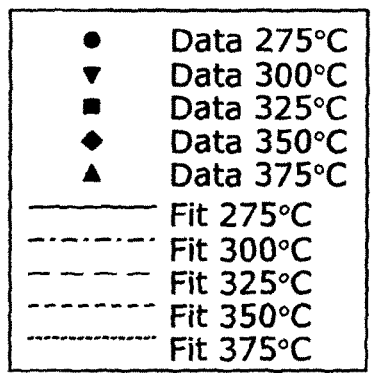
Figure 4: TR1787 data and fitting

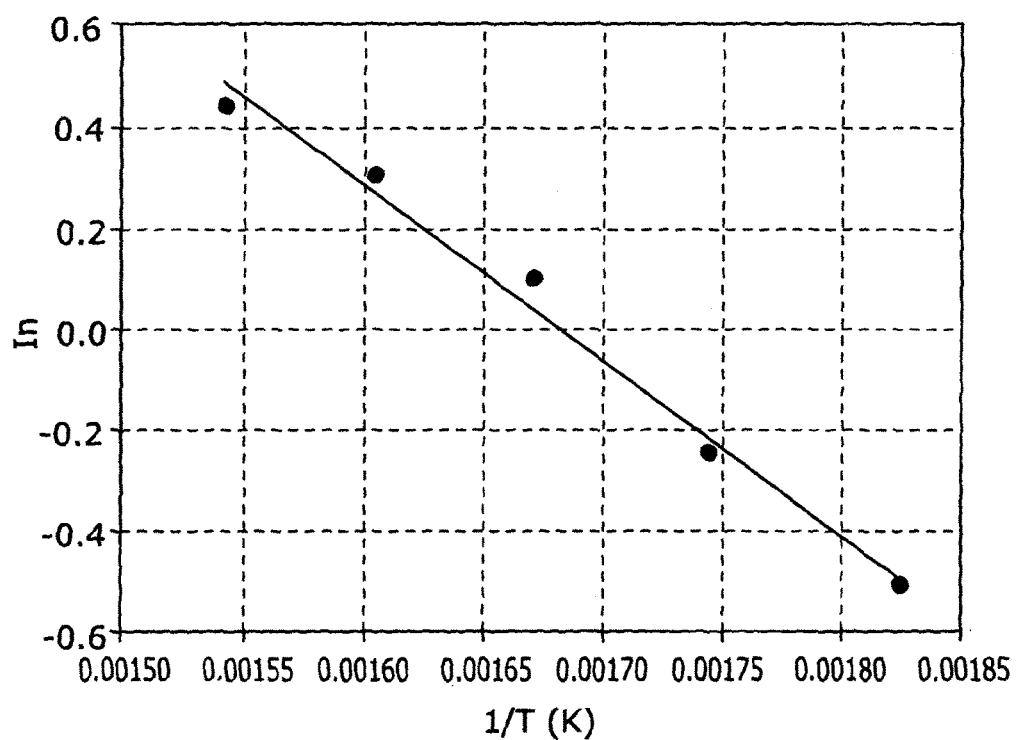
Figure 5: Arrhenius plot

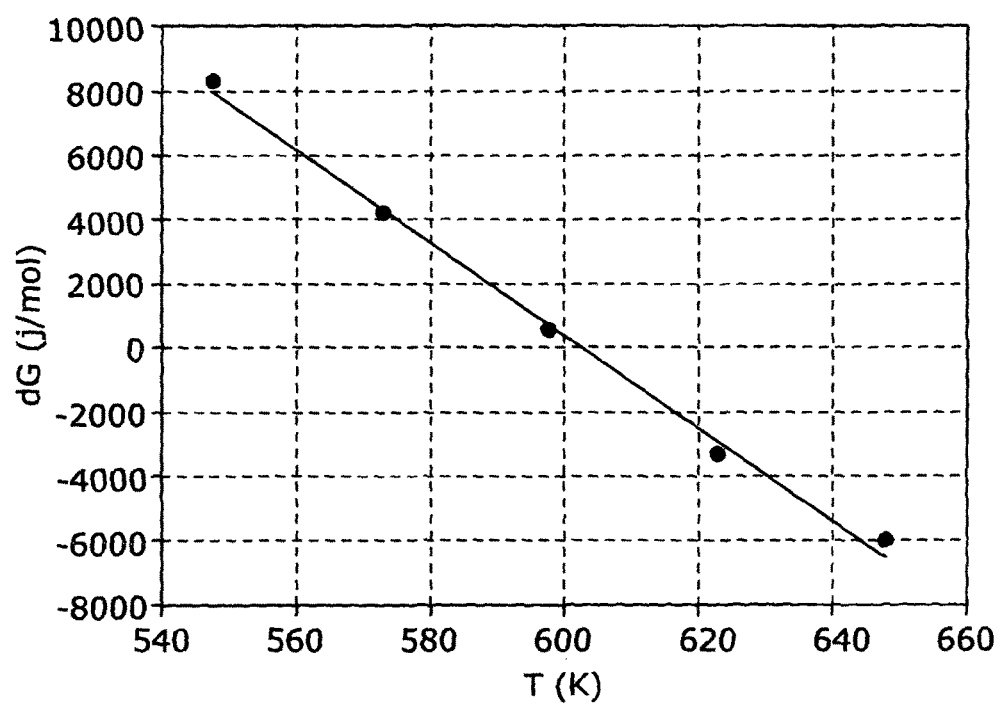
Figure 6: Gibbs plot

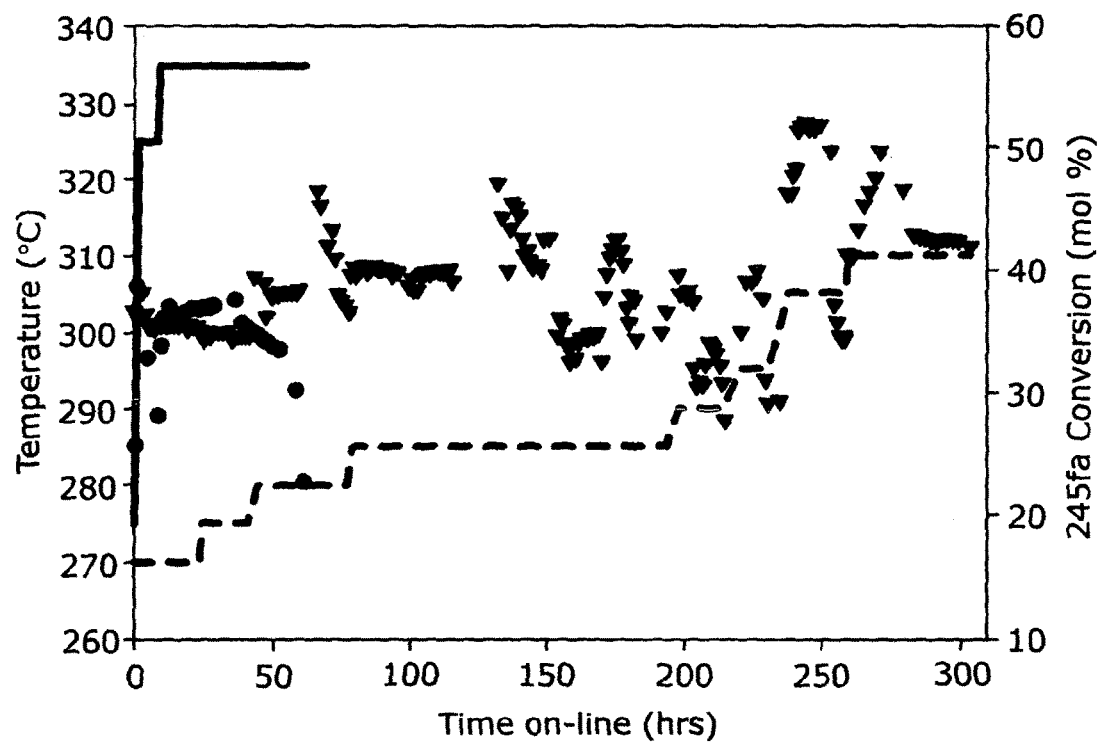
Figure 7: Comparison of Zr and Cr based catalysts

PROCESS FOR PREPARING A C3-C7 (HYDRO) FLUOROALKENE BY DEHYDROHALOGENATION

The present invention relates to a process for preparing (hydro)fluoroalkenes and particularly to a process for preparing $C_{3-7}$ (hydro)fluoroalkenes by the catalytic dehydrohalogenation of $C_{3-7}$ hydro(halo)fluoroalkanes.

The listing or discussion of information or a prior-published document in this specification should not necessarily be taken as an acknowledgement that the information or document is part of the state of the art or is common general knowledge.

$C_{3-7}$ (hydro)fluoroalkenes such a hydrofluoropropenes can be conveniently prepared from corresponding hydro(halo)fluoroalkanes by dehydrohalogenation. The transformation can be effected thermally, i.e. by pyrolysis, catalytically, by contacting a hydro(halo)fluoroalkane with a catalyst under suitable conditions, or chemically, typically by contacting a hydro(halo)fluoroalkane with strong bases such as alkali metal hydroxides. For commercial operation, catalytic dehydrohalogenation is believed to be preferred, and is discussed in more detail below.

The hydrofluoropropene 1,1,1,2,3-pentafluoropropene (HFO-1225ye), for example, can be prepared by contacting and dehydrofluorinating 1,1,1,2,3,3-hexafluoropropane in the gaseous state with trivalent chromium oxide or partially fluorinated trivalent chromium oxide, optionally in the presence of oxygen (see U.S. Pat. No. 5,679,875).

EP-A-1900716 describes the use of a variety of catalysts, including fluorinated chromia, fluorinated alumina, metal fluorides, metal fluorides and carbon-supported transition metals, in the dehydrofluorination of 1,1,3,3,3-pentafluoropropane (HFC-245fa) to 1,3,3,3-tetrafluoropropene (HFO-1234ze).

WO 2008/040969 describes the use of a zinc/chromia catalyst for the preparation of various (hydro)fluoropropenes, including HFO-1225ye and 2,3,3,3-tetrafluoropropene (HFO-1234yf) by dehydrohalogenation of corresponding hydro(halo)fluoropropanes.

Notwithstanding the above processes, catalytic dehydrohalogenation has its problems, one of which is because the chemistry is thought inherently to foul the catalyst. Catalyst fouling typically is controlled by one or more of (a) using the mildest conditions possible, (b) increasing the concentration of hydrogen fluoride, and (c) limiting the exposure of the catalyst to high partial pressure of unsaturates.

The use of measures (b) and (c) above is very limited in the preparation of $C_{3-7}$ (hydro)fluoroalkenes by the catalytic dehydrohalogenation (particularly dehydrofluorination) of $C_{3-7}$ hydro(halo)fluoroalkanes. Consequently, operating cycles and catalyst life are believed generally to be relatively short compared to (hydro)fluorination chemistry. Short operating cycles and catalyst life require more frequent catalyst regeneration, or simply more catalyst, each of which have cost implications. Some catalysts, particularly certain alumina-supported catalysts and/or zirconia-based catalysts, can be difficult to regenerate. This is believed to be because the coke in a used dehydrohalogenation catalyst can be difficult to combust.

Thus, there is a need for an economic process for preparing $C_{3-7}$ (hydro)fluoroalkenes using highly active, stable and regenerable catalysts.

The invention addresses the foregoing and other deficiencies by the provision of a process for preparing a $C_{3-7}$ (hydro)fluoroalkene comprising dehydrohalogenating a $C_{3-7}$ hydro(halo)fluoroalkane in the presence of a catalyst comprising a metal oxide supported on alumina, wherein the catalyst has a sodium content of less than about 800 ppm.

Preferably, the sodium content of the catalyst is less than 500 ppm, more preferably less than 400 ppm, 300 ppm, 200 ppm or 150 ppm. It is especially preferred that the catalyst has a sodium content of less than 100, 80, 60 or 40 ppm. The catalyst used in the catalyst of the invention may contain less than 30, 20 or 10 ppm.

The sodium content can be measured by any suitable known method. Particularly useful methods include atomic absorption (AAS) and optical emission spectroscopy (OES), such as inductively coupled plasma optical emission spectroscopy (ICP-OES). The sodium analysis used in the examples herein was performed by London and Scandanavian Metallurgical Company of Yorkshire, England using ICP-OES.

We refer above to the sodium content of the catalyst. In one embodiment, the amount sodium referred to above corresponds also to sodium content of the alumina support.

This is because, as discussed in more detail below, any sodium that is present in the catalyst typically arises from the preparation of the alumina which forms the support of the catalyst. In other words, the metal oxide (e.g. zirconia) may contain little or no sodium.

In an embodiment, however, there may be measurable sodium content in the metal oxide of the catalyst (as opposed to, or more likely in addition to, any sodium content in the alumina support). For example, chromia typically includes measurable amounts of sodium, for example when the chromia has been made from sodium salts.

Without being bound by theory, it is believed that the low sodium content of the catalysts of the subject invention increases the availability of Lewis acid sites in the catalyst, for example in the alumina support, that are required for the dehydrohalogenation reaction on the invention.

In another embodiment, the catalysts used in the subject invention contain low amounts of other alkali metals and/or low amounts of alkaline earth metals. By "low amounts" we include the amounts referred to above in connection with sodium.

Typically, the catalyst contains at least about 50% by weight of the alumina support, based on the total weight of the catalyst. In one aspect, the catalyst contains at least about 60% by weight of the alumina support, preferably at least about 70% by weight, for example at least about 80% by weight.

The metal oxide typically makes up less than about 50% by weight of the catalyst, based on the total weight of the catalyst. In one embodiment, the catalyst contains up to about 40% by weight of the metal oxide, preferably up to about 30% by weight, for example up to about 20% by weight.

Typically, the metal in the metal oxide is any metal which forms a metal (oxy)fluoride which has Lewis acid character. Examples are metals selected from Sc, Y, Ti, Zr, Hf, V, Nb, Ta, Cr, Mo, W, Mn, Re, Fe, Ru, Co, Rh, Ir, Ni, Pd, Pt, Cu, Ag, Au, Zn, La and Ce.

Preferably, the metal is a transition metal, such as Cr, Zr, Nb, Ta, V, Mo, Ni or Co. In a preferred embodiment, the metal is zirconium or chromium.

The catalyst used in the process of the invention may contain at least one additional metal or compound thereof in addition to the metal oxide. This can also be referred to as a metal promoter. In one embodiment, the at least one additional metal is selected from Sc, Y, Ti, Zr, Hf, V, Nb, Ta, Cr, Mo, W, Mn, Re, Fe, Ru, Co, Rh, Ir, Ni, Pd, Pt, Cu, Ag, Au, Zn, La and Ce. Preferably, the at least one additional metal is selected from Zn, Zr, Cr, In, Co and Ni.

For the avoidance of doubt, the additional metal (or compound thereof) cannot be the same as the metal of the metal oxide for any given catalyst. For example, if the catalyst comprises an oxide of chromium supported on the alumina support, the at least one additional metal can be any suitable metal, including the metals listed in the preceding paragraph, other than chromium.

In a preferred aspect, the compound of the additional metal is an oxide, fluoride or oxyfluoride, of the additional metal.

When present, the total amount of the additional metal or the compound of the additional metal present in the catalysts of the invention is typically from about 0.01% to about 25% by weight, based on the total weight of the catalyst. Preferred amounts of the additional metal or the compound of additional metal are from about 0.1% to about 20%, conveniently from about 0.1% to about 15%. In some embodiments, the catalysts contain the additional metal or the compound of additional metal in an amount of from about 0.5% by weight to about 10% by weight of the catalyst, such as from about 1 to about 8% by weight of the catalyst, e.g. about 1 to about 5% by weight.

It is to be understood that the amount of additional metal or the compound of the additional metal quoted herein refers to the amount of elemental metal, whether present as elemental metal or as a compound of the metal.

Any suitable alumina support may be used for the catalyst providing that it results in a catalyst that has the low amounts of sodium specified herein. Such alumina is available commercially from, for example, BASF or ASM Catalysts LLC. The alumina may be prepared by precipitation from, for example, a solution of ammonia with a suitable aluminium salt, such as aluminium nitrate.

The catalysts used in the subject invention may be made by impregnating commercially available low sodium alumina with the metal oxide, and optionally any additional metal or compound thereof. This may be achieved by any suitable means known in the art of catalyst manufacture, for example by impregnating the alumina with a suitable precursor metal salt or salts from which the metal oxide (and any additional metal or compound thereof) can be readily generated with suitable thermochemical processing.

By way of example, chromia cannot be directly impregnated into alumina. Typically, therefore, a chromium salt is used for impregnation that is soluble in water or another suitable solvent. Suitable chromium salts include chromium (III) nitrate and hexaaquachromium complexes such as $Cr(H_2O)_6.Cl_3$. Following impregnation of the chromium salt in a suitable solvent, and before use, the catalyst is calcined in air and/or nitrogen at temperatures of, for example, 150 to 500° C. An example of the preparation of such a catalyst is described in EP-A-366797, which is incorporated herein by reference.

Alternatively, the catalysts used in the process of the invention may be prepared by co-precipitation of a suitable aluminium precursor salt or salts with a suitable precursor metal salt of the metal oxide (and any additional metal or compound thereof) in a solvent such as water on the addition of ammonia or ammonium hydroxide. Thermochemical processing (e.g. calcining) of the resulting precipitated product yields the desired catalyst.

Another method of preparing the catalysts of the invention is by vapour deposition. This involves impregnating the support by contacting it with the vapours of suitably volatile metal compounds. It may be desirable to heat the support during this contacting to effect decomposition of the vapour, thereby allowing the active metal compound to impregnate the support. Suitably volatile compounds include alkyl compounds such as dimethyl zinc or carbonyl complexes such as chromium hexacarbonyl. See for example, "The design and Preparation of Supported Catalysts", G. J. K. Acres et al, Catalysis, 1981 (RSC), which is incorporated herein by reference.

The low sodium catalysts used in the subject invention contain a metal oxide supported on alumina. Examples include chromia or zirconia supported on (low-sodium) alumina, i.e. chromium oxide or zirconium oxide supported on (low-sodium) alumina. Prior to contacting with the $C_{3-7}$ hydro(halo)fluoroalkane to effect dehydrohalogenation, the catalyst used in the subject invention typically is pre-treated by fluorination. Such pre-treatment is known in the art and generally involves drying the catalyst under nitrogen gas at elevated temperature followed by pre-fluorination with HF (optionally diluted with nitrogen) at elevated temperature.

Consequently, although the original catalyst (also referred to as the pre-catalyst) is a metal oxide (e.g. chromia or zirconia) supported on (low sodium) alumina, the catalyst used at the start of dehydrohalogenation typically is partially or fully fluorinated metal oxide (i.e. a metal oxyfluoride or a metal fluoride) supported on a partially or fully fluorinated low sodium alumina (e.g. an alumina oxyfluoride or alumina fluoride). This is because during pre-treatment at least some of the oxygen atoms in the catalyst are replaced by fluorine atoms. Moreover, in use during the $C_{3-7}$ (hydro)fluoroalkene dehydrohalogenation reaction, the fluorine content of the catalysts is expected to increase.

The catalysts used in the present invention may be amorphous. By this we mean that the catalyst does not demonstrate substantial crystalline characteristics when analysed by, for example, X-ray diffraction. Alternatively, the catalysts may exhibit some crystalline character, in the alumina support and/or the metal oxide.

The catalysts of the invention typically have a surface area of at least 50 $m^2/g$, for example from 50 to about 350 or 400 $m^2/g$, preferably from about 70 to about 250 $m^2/g$, such as from about 100 to about 200 $m^2/g$, before they are subjected to pre-treatment. The pre-fluorination treatment typically has the effect of lowering the surface area of the catalyst. After the pre-fluorination treatment the catalysts of the invention typically have a surface area of from about-1-0 to about 300 $m^2/g$, preferably from about 20 to about 200 $m^2/g$, such as from about 50 to 150 $m^2/g$.

The catalysts of the invention may be provided in any suitable form known in the art. For example, they may be provided in the form of pellets or granules of appropriate size for use in a fixed bed or a fluidised bed.

BRIEF DESCRIPTION OF THE DRAWING FIGURES

FIG. 1 is a graph depicting the conversion of HFC-245fa at various temperatures and various times as discussed in Comparative Example 1.

FIG. 2 is a graph depicting the change of the partial pressure of HFC-245fa over time as discussed in Comparative Example 1.

FIG. 3 is a graph depicting the calculated parameters shown in Table 3 of the specification used to calculate equilibrium constants of the reactions discussed in Comparative Example 1.

FIG. 4 is a graph depicting contact times for the dehydroflourination of HFC-245fa to HFC-1234ze over a low Na/Cr$_2$O$_3$/alumina catalyst, as discussed in Example 2 of the specification.

FIG. 5 is a graph depicting the calculation of an equilibrium constant of Example 2 of the specification.

FIG. 6 is a graph depicting the calculation of an equilibrium constant of Example 2 of the specification.

FIG. 7 is a comparison of Zr and Cr based catalysts effecting HFC-245fa conversion at various temperatures and times.

In use, the catalyst may be regenerated or reactivated periodically by heating in air at a temperature of from about 300° C. to about 500° C. Air may be used as a mixture with an inert gas such as nitrogen or with hydrogen fluoride, which emerges hot from the catalyst treatment process and may be used directly in fluorination processes employing the reactivated catalyst. It has been found that the spent catalyst from the process of the invention typically is unexpectedly easy to regenerate compared to known alumina catalysts. The chromia supported on alumina low sodium catalyst of the invention is believed to be particularly easy to regenerate.

Typically, the process of the invention comprises contacting the C$_{3-7}$ hydro(halo)fluoroalkane with or without added hydrogen fluoride (HF) in the vapour or liquid phase (preferably the vapour phase) and may be carried out at a temperature of from 0 to 400° C., e.g. 50 to 400° C. In certain preferred embodiments, the process may be carried out with no co-feed of HF. The process may be carried out at atmospheric, sub- or super atmospheric pressure, preferably up to about 30 bara, for example from about 1 to about 25 bara.

Preferably, the hydro(halo)fluoroalkane is contacted without HF (e.g. without a HF feed) in the vapour phase at a temperature of from 200 to 360° C., more preferably from 240 to 320° C. Preferably, the process is conducted at a pressure of from 1 to 20 bara. Of course, the skilled person will appreciate that the preferred conditions (e.g. temperature, pressure for conducting the process of the invention may vary (even outside the above ranges) depending on the nature of the hydro(halo)fluoroalkane and (hydro)fluoroalkene, and the catalyst being employed.

The process of the invention can be carried out in any suitable apparatus, such as a static mixer, a stirred tank reactor or a stirred vapour-liquid disengagement vessel. The process may be carried out batch-wise, or continuously. Either the batch-wise process or the continuous process may be carried out in a "one-pot" fashion, or using two or more discrete reaction zones and/or reaction vessels. Of course, even in a "continuous" process, the skilled person will appreciate that the process will need to paused periodically, e.g. for maintenance and/or catalyst regeneration.

The dehydrofluorination can be carried out in the absence of an HF feed but it may be desirable in certain embodiments to use some HF in order to prevent and/or retard excessive decomposition of the organic feed and/or coking of the catalyst. Typically, the HF:organics ratio in the process of the invention if an HF feed is utilised will range from about 0.01:1 to about 1:1, preferably from about 0.1:1 to about 1:1, more preferably from about 0.5:1 to about 1:1.

Unless otherwise stated, as used herein, a (hydro)fluoroalkene is an alkene in which at least one of the hydrogen atoms has been replaced by fluorine.

Unless otherwise stated, as used herein, a hydro(halo)fluoroalkane is an alkane in which at least one but not all hydrogen atom has been replaced by a fluorine atom and optionally at least one hydrogen atom has been replaced by a halogen selected from chlorine, bromine and iodine. Thus, hydro(halo)fluoroalkanes contain at least one hydrogen, at least one fluorine and optionally at least one halogen selected from chlorine, bromine and iodine. In other words, the definition of a hydro(halo)fluoroalkane includes a hydrofluoroalkane, i.e., an alkane in which at least one but not all of the hydrogen atoms have been replaced by fluorine.

For the avoidance of doubt, as used herein, any reference to a C$_{3-7}$ (hydro)fluoroalkene, hydrofluoroalkane or hydro(halo)fluoroalkane refers to a (hydro)fluoroalkene, hydrofluoroalkane or hydro(halo)fluoroalkane having from 3 to 7 carbon atoms, i.e. hydro(halo)fluoro-propane, butane, pentane, hexane or heptane or a (hydro)fluoro-propene, butene, pentene, hexane or heptene.

The (hydro)fluoroalkenes produced by the process of the invention contain a double bond and may thus exist as E (entgegen) and Z (zusammen) geometric isomers about each individual double bond. All such isomers and mixtures thereof are included within the scope of the invention.

Unless otherwise stated, as used herein, by the term "dehydrohalogenation" (or dehydrohalogenating), we refer to the removal of hydrogen halide (e.g. HF, HCl, HBr or HI), for example from a hydro(halo)fluoroalkane. Thus the term "dehydrohalogenation" includes "dehydrofluorination", "dehydrochlorination", "dehydrobromination" and "dehydroiodination" of a hydro(halo)fluoroalkane.

The process of the invention is suitable for preparing any C$_{3-7}$ (hydro)fluoroalkene by dehydrohalogenating (e.g. dehydrofluorinating or dehydrochlorinating) a C$_{3-7}$ hydro(halo)fluoroalkane. Optionally, the C$_{3-7}$ hydro(halo)fluoroalkane may first be fluorinated to a C$_{3-7}$ hydrofluoroalkane which may then be dehydrofluorinated to a C$_{3-7}$ (hydro)fluoroalkene.

Preferably, the C$_{3-7}$ (hydro)fluoroalkene is a (hydro)fluoropropene prepared by the dehydrohalogenation of a hydro(halo)fluoropropane. The invention is particularly suited to the preparation of (hydro)fluoropropenes and (hydro)fluorobutenes, especially (hydro)fluoropropenes.

By way of example and for simplicity, unless otherwise stated, the remainder of the specification will describe the process of the invention with reference to the preparation of (hydro)fluoropropenes. The skilled person will understand that such discussion is equally applicable to the preparation of C$_{4-7}$ (hydro)fluoroalkenes.

(Hydro)fluoropropenes prepared by the process of the invention may contain 0, 1, 2, 3, 4 or 5 hydrogen atoms and 1, 2, 3, 4, 5 or 6 fluorine atoms. Preferred (hydro)fluoropropenes are those having from 3 to 5 fluorine atoms (and thus from 1 to 3 hydrogen atoms), particularly 4 or 5 fluorine atoms (and thus 1 or 2 hydrogen atoms). In other words, preferred (hydro)fluoropropenes are trifluoropropenes, tetrafluoropropenes and pentafluoropropenes, particularly tetrafluoropropenes and pentafluoropropenes, and especially tetrafluoropropenes.

A preferred trifluropropene prepared by the process of the invention is 3,3,3-trifluoropropene (HFO-1243zf).

1,3,3,3-tetrafluoropropene (HFO-1234ze, both cis and trans isomers) and 2,3,3,3-tetrafluoropropene (HFO-1234yf) are preferred tetrafluoropropenes that are prepared by the process of the invention.

A preferred pentafluoropropene prepared by the process of the invention is 1,2,3,3,3-pentafluoropropene (HFO-1225ye, both cis and trans isomers).

The (hydro)fluoropropenes which can be made by the process of the invention may be prepared starting from one or more of a large number of hydro(halo)fluoropropanes.

HFO-1243zf can be conveniently prepared by dehydrohalogenation of compounds of the type $CF_3CH_2CH_2X$, where X is a halogen (F, Cl, Br, I). Particularly preferred are compound of this type where X is F or Cl, namely $CF_3CH_2CH_2F$ (HFC-254fb) or $CF_3CH_2CH_2Cl$ (HFC-253fb).

In a preferred embodiment, HFO-1234yf is prepared by dehydrofluorination of 1,1,1,2,2-pentafluoropropane (HFC-245cb) or 1,1,1,2,3-pentafluoropropane (HFC-245ea).

Preferably, HFO-1234ze is prepared by dehydrofluorination of 1,1,1,3,3-pentafluoropropane (HFC-245fa).

In a preferred aspect, HFO-1225ye is prepared by dehydrofluorination of 1,1,1,2,3,3-hexafluoropropane (HFC-236ea).

The invention is illustrated by the following non-limiting Examples.

COMPARATIVE EXAMPLE 1

Dehydrofluorination of 245fa to 1234ze (High Na $ZrO_2$/Alumina)

This example describes the dehydrofluorination of HFC-245fa to HFO-1234ze using a high sodium alumina supported zirconium catalyst.

Catalyst Preparation 50 ml (39.2925 g) of alumina spheres (obtained from Aldrich with a sodium content of 2340 ppm having a diameter of 5 mm and a surface area of 310 m²/g) were impregnated overnight with a solution of zirconium (IV) oxychloride octahydrate (10.4467 g) in absolute ethanol (463 g). The ethanol was then distilled off under vacuum and finally the catalyst was dried at 150° C. again under vacuum. The catalyst Zr loading, as prepared, was nominally 7.5% wt/wt (the actual Zr loading of the catalyst was measured and found to be 1.81% wt/wt) and the surface area of the impregnated catalyst was 251.33 m²/g.

Catalyst Testing

The Zr/alumina catalyst was tested at atmospheric pressure using a neat 245fa feed. The atmospheric test apparatus was equipped with 2 reactor tubes, each with independent HF, organic and nitrogen feeds. For this study each reactor tube was loaded with the catalyst described above (reactor A 5 ml, reactor B 2 ml). The catalyst in both reactors was first dried under nitrogen (60 ml/min) at 200° C. for 72 hours. They were then pre-fluorinated with HF diluted in nitrogen (30 ml/min HF and 20 ml/min $N_2$) at 200° C. for 1 hour. At this point the nitrogen flow was stopped and the catalysts treated with neat HF and the temperature ramped from 200° C. to 450° C. at 40° C./hr. These conditions were maintained for a further hour before the catalysts were cooled to 200° C. The HF flow was then stopped and replaced with a nitrogen flow (60 ml/min), the catalysts were ready for use when no further HF was detected in the reactor off-gases.

245fa (20 ml/min) was then fed to reactor (A) and the reactor temperature adjusted until a 245fa conversion of c.a. 40% was achieved. These conditions were maintained and the reactor off-gases periodically sampled. When necessary the reactor temperature was increased so as to maintain the 245fa conversion around the 40% target level up to an arbitrary limit of 340° C. 245fa (10-30 ml/min) was also fed to reactor (B) and conversion and yields determined as a function of temperature and contact time.

The experiment was performed at atmospheric pressure without an HF co-feed. The results are presented in Table 1 and illustrated in FIG. 1.

TABLE 1

Catalyst Performance and Stability Testing Results

| Temperature (° C.) | Time on-line (hrs) | E-1234ze (mol %) | Z-1234ze (mol %) | 245fa (mol %) | 245fa Conversion (%) | Ratio E:Z |
|---|---|---|---|---|---|---|
| 250 | −1 | 17.0 | 3.4 | 79.6 | 20.4 | 4.9 |
| 250 | −0.45 | 12.5 | 2.4 | 85.1 | 14.9 | 5.1 |
| 275 | −0.5 | 19.7 | 4.2 | 76.1 | 23.9 | 4.7 |
| 275 | −0.25 | 20.5 | 4.3 | 75.3 | 24.7 | 4.8 |
| 300 | 0 | 30.6 | 6.8 | 62.6 | 37.4 | 4.5 |
| 300 | 0.15 | 34.6 | 7.8 | 57.6 | 42.4 | 4.4 |
| 300 | 0.3 | 34.1 | 7.8 | 58.1 | 41.9 | 4.4 |
| 300 | 18 | 43.3 | 9.4 | 47.3 | 52.7 | 4.6 |
| 300 | 19 | 34.2 | 7.5 | 58.4 | 41.6 | 4.6 |
| 300 | 20 | 32.7 | 7.1 | 60.2 | 39.8 | 4.6 |
| 325 | 23 | 48.4 | 11.1 | 40.5 | 59.5 | 4.4 |
| 320 | 24 | 43.4 | 10.4 | 46.3 | 53.7 | 4.2 |
| 325 | 25 | 47.8 | 10.5 | 41.7 | 58.3 | 4.6 |
| 325 | 42 | 42.2 | 9.9 | 47.9 | 52.1 | 4.3 |
| 325 | 58 | 41.3 | 9.8 | 48.9 | 51.1 | 4.2 |
| 325 | 59 | 40.1 | 9.4 | 50.5 | 49.5 | 4.3 |
| 330 | 60 | 54.2 | 13.3 | 32.5 | 67.5 | 4.1 |
| 330 | 64 | 46.9 | 11.3 | 41.7 | 58.3 | 4.1 |
| 330 | 80 | 37.7 | 9.0 | 53.3 | 46.7 | 4.2 |
| 330 | 82 | 26.5 | 6.1 | 67.4 | 32.6 | 4.3 |
| 325 | 83 | 18.8 | 4.1 | 77.1 | 22.9 | 4.5 |
| 325 | 83.5 | 19.8 | 4.4 | 75.8 | 24.2 | 4.5 |
| 325 | 85 | 32.6 | 7.6 | 59.7 | 40.3 | 4.3 |
| 325 | 86 | 34.2 | 8.1 | 57.7 | 42.3 | 4.2 |
| 330 | 87 | 39.9 | 9.1 | 51.0 | 49.0 | 4.4 |
| 330 | 88 | 37.6 | 8.6 | 53.8 | 46.2 | 4.4 |
| 330 | 89 | 35.9 | 8.7 | 55.4 | 44.6 | 4.1 |
| 335 | 105 | 47.9 | 10.3 | 41.8 | 58.2 | 4.7 |
| 335 | 106 | 51.2 | 10.1 | 38.7 | 61.3 | 5.1 |
| 335 | 108 | 43.3 | 9.1 | 47.6 | 52.4 | 4.8 |
| 335 | 109 | 21.5 | 4.3 | 74.2 | 25.8 | 4.9 |
| 340 | 110 | 31.5 | 7.5 | 61.0 | 39.0 | 4.2 |
| 340 | 111 | 24.5 | 5.5 | 70.0 | 30.0 | 4.4 |
| 340 | 127 | 31.0 | 6.9 | 62.0 | 38.0 | 4.5 |
| 340 | 128 | 35.9 | 8.9 | 55.2 | 44.8 | 4.0 |
| 340 | 129 | 35.6 | 8.6 | 55.8 | 44.2 | 4.1 |
| 340 | 130 | 36.5 | 8.8 | 54.7 | 45.3 | 4.1 |
| 340 | 146 | 32.9 | 8.2 | 58.9 | 41.1 | 4.0 |
| 340 | 147 | 32.4 | 7.8 | 59.8 | 40.2 | 4.1 |
| 340 | 149 | 30.3 | 7.3 | 62.4 | 37.6 | 4.2 |
| 340 | 166 | 35.5 | 8.9 | 55.6 | 44.4 | 4.0 |
| 340 | 167 | 26.9 | 6.7 | 66.5 | 33.5 | 4.0 |
| 340 | 168 | 27.4 | 6.7 | 65.9 | 34.1 | 4.1 |
| 340 | 170 | 27.4 | 6.7 | 65.9 | 34.1 | 4.1 |
| 340 | 186 | 29.6 | 7.3 | 63.1 | 36.9 | 4.1 |
| 340 | 188 | 30.3 | 7.1 | 62.5 | 37.5 | 4.3 |
| 340 | 190 | 23.3 | 4.8 | 71.9 | 28.1 | 4.8 |
| 340 | 197 | 25.2 | 6.2 | 68.6 | 31.4 | 4.0 |
| 340 | 213 | 20.1 | 5.1 | 74.8 | 25.2 | 4.0 |

The reaction commenced immediately at 250° C. yielding a mixture of unreacted 245fa and the E and Z isomers of 1234ze, as expected. The target 245fa conversion was achieved at c.a. 300° C. This conversion was maintained for c.a. 213 hours by ramping the temperature ultimately to 340° C., the limit for this experiment. In normal operation no by-products were detected as they were below the detection limits for the GC analytical method. However, more concentrated samples were periodically taken and in these it was possible to detect, although not quantify, the by-products trifluoromethyl acetylene and 1234zc ($F_2C=CH_2CHF_2$). There was considerable scatter in the data but this tended to coincide with feed upsets caused e.g. following topping up of the feed reservoir or following breaks caused by weekends etc. Allowing for the peaks and troughs caused by these upsets it would appear that the performance of the catalyst slowly deteriorated over the 213 hours of the experiment.

By integration of the data in Table 1 it can be shown that over the course of the 213 hours of the experiment the mean 245fa conversion was 43.7%. The mean selectivity to E-1234ze was 81% and therefore the mean ratio of E:Z isomers was 4.26:1. At 1 m³ (of catalyst) scale the mean E-1234ze production rate would have been equivalent to 0.47 to/hr. At the end of the 213 hours the surface area of the catalyst was measured at 27.8 m²/g and the coke level on the catalyst was measured by TGA to be 2.1% wt and the coke was very resistant to combustion.

In situ regeneration of the catalyst was attempted in the reactor at 340, 380 and 450° C. with air (3 ml/min) diluted in nitrogen (60 ml/min). Whilst these regenerations combined were effective in removing the coke they were not effective in returning the activity the catalyst to anything like its initial activity. Thus, the lifetime of this alumina supported catalyst was limited to 1 operating cycle.

Temperature and Contact Time Studies

The aim of this experiment was to measure the response of the reaction to changes in temperature and contact time and use the data to explore the underlying kinetics and thermodynamics of the reaction. In order that the reactor approximated to differential conditions a relatively small catalyst charge was used with short contact times. The data is summarised in Table 2.

It was found that the kinetic expression that best fitted all the data sets was that for the complex equilibrium A=B+C:

$$\frac{dC}{dt} = -k\frac{(C_{A_O}^2 - C_{A_e}C)(C_{A_e} - C)}{(C_{A_O} - C_{A_e})^2}$$

The quality of the fits to the data obtained using this rate law can be appreciated by inspection of FIG. 2. By fitting each data set to this equation it was possible to determine net rate constants and equilibrium 245fa, 1234ze and HF levels. The rate constants were used to calculate the Arrhenius parameters of the reaction and the equilibrium data used to calculate equilibrium constants. These were then used to determine the free energy of reaction and subsequently the heat and entropy of reaction. Consequently, by using the Vant Hoff equation it was possible to calculate the equilibrium constant at any temperature. Key data and calculated parameters are presented in Table 3 and illustrated in FIG. 3.

TABLE 2

Temperature and Contact Time Data

| 245fa Feed (ml/min) | Temp. (° C.) | Mean Contact Time (s) | 245fa (bara) | 1234ze (bara) | HF (bara) | E-1234ze (mol %) | Z-1234ze (mol %) |
|---|---|---|---|---|---|---|---|
| 10 | 275 | 5.48 | 0.45 | 0.28 | 0.28 | 31.57 | 6.47 |
| 20 | 275 | 2.86 | 0.56 | 0.22 | 0.22 | 23.70 | 4.86 |
| 30 | 275 | 1.96 | 0.64 | 0.18 | 0.18 | 18.02 | 3.66 |
| 10 | 300 | 5.02 | 0.35 | 0.33 | 0.33 | 40.10 | 8.59 |
| 20 | 300 | 2.61 | 0.44 | 0.28 | 0.28 | 32.16 | 7.02 |
| 30 | 300 | 1.83 | 0.57 | 0.22 | 0.22 | 22.61 | 4.88 |
| 10 | 325 | 4.50 | 0.21 | 0.40 | 0.40 | 53.75 | 12.11 |
| 20 | 325 | 2.34 | 0.29 | 0.36 | 0.36 | 44.75 | 10.33 |
| 30 | 325 | 1.64 | 0.40 | 0.30 | 0.30 | 34.62 | 7.97 |
| 10 | 350 | 4.13 | 0.13 | 0.44 | 0.44 | 63.25 | 14.43 |
| 20 | 350 | 2.14 | 0.19 | 0.41 | 0.41 | 55.08 | 13.36 |
| 30 | 350 | 1.48 | 0.26 | 0.37 | 0.37 | 48.04 | 11.28 |
| 10 | 375 | 3.91 | 0.10 | 0.45 | 0.45 | 65.90 | 16.31 |
| 20 | 375 | 2.00 | 0.14 | 0.43 | 0.43 | 59.98 | 15.31 |
| 30 | 375 | 1.41 | 0.24 | 0.38 | 0.38 | 48.26 | 12.48 |

| | | 245fa (mol %) | 245fa (ml/min) | 1234ze (ml/min) | HF (ml/min) | Sum (ml/min) | Mean flow (ml/min) |
|---|---|---|---|---|---|---|---|
| 10 | 275 | 61.96 | 6.20 | 3.80 | 3.80 | 13.80 | 11.90 |
| 20 | 275 | 71.43 | 14.29 | 5.71 | 5.71 | 25.71 | 22.86 |
| 30 | 275 | 78.32 | 23.50 | 6.50 | 6.50 | 36.50 | 33.25 |
| 10 | 300 | 51.31 | 5.13 | 4.87 | 4.87 | 14.87 | 12.43 |
| 20 | 300 | 60.82 | 12.16 | 7.84 | 7.84 | 27.84 | 23.92 |
| 30 | 300 | 72.51 | 21.75 | 8.25 | 8.25 | 38.25 | 34.12 |
| 10 | 325 | 34.14 | 3.41 | 6.59 | 6.59 | 16.59 | 13.29 |
| 20 | 325 | 44.92 | 8.98 | 11.02 | 11.02 | 31.02 | 25.51 |
| 30 | 325 | 57.41 | 17.22 | 12.78 | 12.78 | 42.78 | 36.39 |
| 10 | 350 | 22.33 | 2.23 | 7.77 | 7.77 | 17.77 | 13.88 |
| 20 | 350 | 31.56 | 6.31 | 13.69 | 13.69 | 33.69 | 26.84 |
| 30 | 350 | 40.68 | 12.20 | 17.80 | 17.80 | 47.80 | 38.90 |
| 10 | 375 | 17.79 | 1.78 | 8.22 | 8.22 | 18.22 | 14.11 |
| 20 | 375 | 24.71 | 4.94 | 15.06 | 15.06 | 35.06 | 27.53 |
| 30 | 375 | 39.25 | 11.78 | 18.22 | 18.22 | 48.22 | 39.11 |

TABLE 3

Kinetic and thermodynamic parameters

| Temperature (° C.) | Temperature (K) | 1/T (K) | Ln $k_n$ | $[245fa]_{eq}$ (bara) | $[1234ze]_{eq}$ (bara) |
|---|---|---|---|---|---|
| 275 | 548 | 0.001825 | −1.41634 | 0.4186 | 0.2907 |
| 300 | 573 | 0.001745 | −1.03423 | 0.30906 | 0.34547 |
| 325 | 598 | 0.001672 | −0.47626 | 0.21 | 0.395 |
| 350 | 623 | 0.001605 | 0.03999 | 0.1247 | 0.43765 |
| 375 | 648 | 0.001543 | 0.11489 | 0.0867 | 0.45665 |

| | $[HF]_{eq}$ (bara) | $K_{eq}$ | Ln $K_{eq}$ | $\Delta G_r$ (J/mol) |
|---|---|---|---|---|
| 275 | 0.2907 | 0.201879 | −1.60009 | 7290.114 |
| 300 | 0.34547 | 0.386169 | −0.95148 | 4532.772 |
| 325 | 0.395 | 0.742976 | −0.29709 | 1477.07 |
| 350 | 0.43765 | 1.535987 | 0.429173 | −2222.95 |
| 375 | 0.45665 | 2.405181 | 0.877625 | −4728.18 |

From the Arrhenius plot illustrated in FIG. 3 it was possible to calculate that:

Activation energy ($E_{act}$)=55.7 kJ/mol
Ln Pre-exponential factor (Ln A)=10.756

Similarly from the plot of $dG_r$ versus temperature it was possible to calculate that:

Heat of reaction ($dH_r$)=+74.76 kJ/mol
Entropy of reaction ($dS_1$)=+123.17 J/mol.K Therefore, the equilibrium constant at any temperature can be calculated using the Vant Hoff equation:

$$K = \text{Exp}\left[\frac{dH}{RT} - \frac{dS}{R}\right]$$

EXAMPLE 2

Dehydrofluorination of 245fa to 1234ze (Low Na $Cr_2O_3$/Alumina)

The catalyst used for this Example was an alumina supported chromia catalyst (denoted TR1787) containing 111 ppm sodium and having a surface area of 140.6 m²/g, for the dehydrofluorination of 245fa.

The catalyst was tested at atmospheric pressure using a neat 245fa feed. For catalyst screening and kinetic studies, the reactor was charged with 2 ml of catalyst, which was first dried under nitrogen (60 ml/min) at 200° C. for 72 hours. It was then pre-fluorinated with HF diluted in nitrogen (30 ml/min HF and 20 ml/min $N_2$) at 200° C. for 1 hour. At this point the nitrogen flow was stopped and the catalyst treated with neat HF and the temperature ramped from 200° C. to 450° C. at 40° C./hr. These conditions were maintained for a further hour before the catalyst was cooled to 200° C. The HF flow was then stopped and replaced with a nitrogen flow (60 ml/min), the catalyst was ready for use when no further HF was detected in the reactor off-gases. The data obtained is summarised in Tables 4 and 5 and illustrated in FIG. 4.

TABLE 4

TR1787 data

| Temp (Deg C.) | Mean CT (sec) | 245fa (bara) | 1234ze (bara) | HF (bara) | Sum (bara) | 245fa in (ml/min) | 1234zeE (mol %) |
|---|---|---|---|---|---|---|---|
| 275 | 22.01 | 0.46 | 0.27 | 0.27 | 1.00 | 2.5 | 31.36 |
| 275 | 10.95 | 0.45 | 0.28 | 0.28 | 1.00 | 5 | 32.60 |
| 275 | 5.48 | 0.45 | 0.28 | 0.28 | 1.00 | 10 | 32.41 |
| 275 | 2.77 | 0.48 | 0.26 | 0.26 | 1.00 | 20 | 29.83 |
| 275 | 1.87 | 0.51 | 0.24 | 0.24 | 1.00 | 30 | 27.15 |
| 275 | 0.95 | 0.56 | 0.22 | 0.22 | 1.00 | 60 | 23.67 |
| | 1243zeZ (mol %) | 245fa (mol %) | 245fa (ml/min) | 1234ze (ml/min) | HF (ml/min) | Sum (ml/min) | Mean flow (ml/min |
| 275 | 5.87 | 62.78 | 1.57 | 0.93 | 0.93 | 3.43 | 2.97 |
| 275 | 5.79 | 61.61 | 3.08 | 1.92 | 1.92 | 6.92 | 5.96 |
| 275 | 5.79 | 61.80 | 6.18 | 3.82 | 3.82 | 13.82 | 11.91 |
| 275 | 5.49 | 64.68 | 12.94 | 7.06 | 7.06 | 27.06 | 23.53 |
| 275 | 5.05 | 67.80 | 20.34 | 9.66 | 9.66 | 39.66 | 34.83 |
| 275 | 4.41 | 71.92 | 43.15 | 16.85 | 16.85 | 76.85 | 68.43 |
| | Mean CT (sec) | 245fa (bara) | 1234ze (bara) | HF (bara) | Sum (bara) | 245fa in (ml/min) | 1243ze E (mol %) |
| 300 | 19.62 | 0.29 | 0.35 | 0.35 | 1.00 | 2.5 | 45.83 |
| 300 | 9.83 | 0.30 | 0.35 | 0.35 | 1.00 | 5 | 45.43 |
| 300 | 4.92 | 0.30 | 0.35 | 0.35 | 1.00 | 10 | 44.82 |
| 300 | 2.51 | 0.34 | 0.33 | 0.33 | 1.00 | 20 | 40.52 |
| 300 | 1.71 | 0.39 | 0.30 | 0.30 | 1.00 | 30 | 36.11 |
| 300 | 0.90 | 0.52 | 0.24 | 0.24 | 1.00 | 60 | 26.33 |
| | 1243zeZ (mol %) | 245fa (mol %) | 245fa (ml/min) | 1234ze (ml/min) | HF (ml/min) | Sum (ml/min) | Mean flow (ml/min |
| 300 | 8.68 | 45.48 | 1.14 | 1.36 | 1.36 | 3.86 | 3.18 |
| 300 | 8.40 | 46.17 | 2.31 | 2.69 | 2.69 | 7.69 | 6.35 |
| 300 | 8.76 | 46.42 | 4.64 | 5.36 | 5.36 | 15.36 | 12.68 |
| 300 | 8.21 | 51.26 | 10.25 | 9.75 | 9.75 | 29.75 | 24.87 |
| 300 | 7.41 | 56.48 | 16.94 | 13.06 | 13.06 | 43.06 | 36.53 |
| 300 | 5.51 | 68.16 | 40.90 | 19.10 | 19.10 | 79.10 | 69.55 |

TABLE 4-continued

TR1787 data

| | Mean CT (sec) | 245fa (bara) | 1234ze (bara) | HF (bara) | Sum (bara) | 245fa in (ml/min) | 1243ze E (mol %) |
|---|---|---|---|---|---|---|---|
| 325 | 17.82 | 0.19 | 0.41 | 0.41 | 1.00 | 2.5 | 57.17 |
| 325 | 8.89 | 0.18 | 0.41 | 0.41 | 1.00 | 5 | 57.45 |
| 325 | 4.47 | 0.19 | 0.40 | 0.40 | 1.00 | 10 | 56.04 |
| 325 | 2.27 | 0.22 | 0.39 | 0.39 | 1.00 | 20 | 52.60 |
| 325 | 1.54 | 0.26 | 0.37 | 0.37 | 1.00 | 30 | 48.30 |
| 325 | 0.82 | 0.38 | 0.31 | 0.31 | 1.00 | 60 | 36.30 |

| | 1243zeZ (mol %) | 245fa (mol %) | 245fa (ml/min) | 1234ze (ml/min) | HF (ml/min) | Sum (ml/min) | Mean flow (ml/min |
|---|---|---|---|---|---|---|---|
| 325 | 11.32 | 31.51 | 0.79 | 1.71 | 1.71 | 4.21 | 3.36 |
| 325 | 11.60 | 30.94 | 1.55 | 3.45 | 3.45 | 8.45 | 6.73 |
| 325 | 11.81 | 32.15 | 3.21 | 6.79 | 6.79 | 16.79 | 13.39 |
| 325 | 11.40 | 36.00 | 7.20 | 12.80 | 12.80 | 32.80 | 26.40 |
| 325 | 10.56 | 41.14 | 12.34 | 17.66 | 17.66 | 47.66 | 38.83 |
| 325 | 8.12 | 55.57 | 33.34 | 26.66 | 26.66 | 86.66 | 73.33 |

| | Mean CT (sec) | 245fa (bara) | 1234ze (bara) | HF (bara) | Sum (bara) | 245fa in (ml/min) | 1243ze E (mol %) |
|---|---|---|---|---|---|---|---|
| 350 | 16.46 | 0.12 | 0.44 | 0.44 | 1.00 | 2.5 | 65.66 |
| 350 | 8.20 | 0.11 | 0.44 | 0.44 | 1.00 | 5 | 66.17 |
| 350 | 4.10 | 0.11 | 0.44 | 0.44 | 1.00 | 10 | 65.64 |
| 350 | 2.08 | 0.14 | 0.43 | 0.43 | 1.00 | 20 | 61.64 |
| 350 | 1.43 | 0.19 | 0.40 | 0.40 | 1.00 | 30 | 54.87 |
| 350 | 0.80 | 0.44 | 0.28 | 0.28 | 1.00 | 60 | 32.27 |

| | 1243zeZ (mol %) | 245fa (mol %) | 245fa (ml/min) | 1234ze (ml/min) | HF (ml/min) | Sum (ml/min) | Mean flow (ml/min |
|---|---|---|---|---|---|---|---|
| 350 | 13.25 | 21.08 | 0.53 | 1.97 | 1.97 | 4.47 | 3.49 |
| 350 | 13.99 | 19.84 | 0.99 | 4.01 | 4.01 | 9.01 | 7.00 |
| 350 | 14.41 | 19.95 | 1.99 | 8.01 | 8.01 | 18.01 | 14.00 |
| 350 | 13.91 | 24.45 | 4.89 | 15.11 | 15.11 | 35.11 | 27.56 |
| 350 | 12.65 | 32.48 | 9.74 | 20.26 | 20.26 | 50.26 | 40.13 |
| 350 | 6.64 | 61.09 | 36.66 | 23.34 | 23.34 | 83.34 | 71.67 |

| | Mean CT (sec) | 245fa (bara) | 1234ze (bara) | HF (bara) | Sum (bara) | 245fa in (ml/min) | 1243ze E (mol %) |
|---|---|---|---|---|---|---|---|
| 375 | 15.43 | 0.07 | 0.46 | 0.46 | 1.00 | 2.5 | 71.29 |
| 375 | 7.68 | 0.07 | 0.47 | 0.47 | 1.00 | 5 | 71.45 |
| 375 | 3.84 | 0.07 | 0.47 | 0.47 | 1.00 | 10 | 70.65 |
| 375 | 1.97 | 0.11 | 0.44 | 0.44 | 1.00 | 20 | 64.40 |
| 375 | 1.37 | 0.19 | 0.41 | 0.41 | 1.00 | 30 | 55.24 |
| 375 | 0.74 | 0.34 | 0.33 | 0.33 | 1.00 | 60 | 39.22 |

| | 1243zeZ (mol %) | 245fa (mol %) | 245fa (ml/min) | 1234ze (ml/min) | HF (ml/min) | Sum (ml/min) | Mean flow (ml/min |
|---|---|---|---|---|---|---|---|
| 375 | 14.86 | 13.85 | 0.35 | 2.15 | 2.15 | 4.65 | 3.58 |
| 375 | 15.94 | 12.60 | 0.63 | 4.37 | 4.37 | 9.37 | 7.18 |
| 375 | 16.69 | 12.65 | 1.27 | 8.73 | 8.73 | 18.73 | 14.37 |
| 375 | 15.46 | 20.14 | 4.03 | 15.97 | 15.97 | 35.97 | 27.99 |
| 375 | 13.33 | 31.43 | 9.43 | 20.57 | 20.57 | 50.57 | 40.28 |
| 375 | 9.63 | 51.16 | 30.69 | 29.31 | 29.31 | 89.31 | 74.65 |

TABLE 5

TR1787 Kinetic and Thermodynamic Data

| Deg C. | K | 1/K | ln k | k (s$^{-1}$) | [245fa]$_{eq}$ (bara) | [1234ze]$_{eq}$ (bara) | [HF]$_{eq}$ (bara) | K$_{eq}$ | ln K$_{eq}$ | ΔG$_r$ (J/mol) |
|---|---|---|---|---|---|---|---|---|---|---|
| 275 | 548 | 0.001825 | −0.51083 | 0.6 | 0.455 | 0.2725 | 0.2725 | 0.163201 | −1.81278 | 8259.136 |
| 300 | 573 | 0.001745 | −0.24846 | 0.78 | 0.295 | 0.3525 | 0.3525 | 0.421208 | −0.86463 | 4119.027 |
| 325 | 598 | 0.001672 | 0.09531 | 1.1 | 0.185 | 0.4075 | 0.4075 | 0.897601 | −0.10803 | 537.0967 |
| 350 | 623 | 0.001605 | 0.300105 | 1.35 | 0.105 | 0.4475 | 0.4475 | 1.907202 | 0.645637 | −3344.16 |
| 375 | 648 | 0.001543 | 0.438255 | 1.55 | 0.07 | 0.465 | 0.465 | 3.088929 | 1.127824 | −6076.12 |

The quality of the fits of the equilibrium rate law to the data was excellent, further confirming its validity in describing the kinetics of the 245fa→1234ze reaction described above. It was clear in each case that the reaction had reached equilibrium at each temperature used in the study. This data was used to calculate the Arrhenius parameters associated with the TR1787 catalysed reaction and to estimate of the enthalpy and entropy of reaction.

FIGS. 5 and 6 illustrate the fits of the Arrhenius, Gibbs, and Van't Hoff equations to the relevant data and from these fits were calculated activation energy, pre-exponential factor, enthalpy and entropy of the reaction, see Table 6.

TABLE 6

Kinetic and thermodynamic parameters

| Parameter | New estimate | Old estimate (Example 1) |
|---|---|---|
| Activation energy ($E_{act}$) | 29041.2 J/mol | N/A |
| Pre-exponential factor (A) | 356.59 s$^{-1}$ | N/A |
| $\Delta H_r$ (Gibbs) | 87130.81 J/mol | 74760 J/mol |
| $\Delta S_r$ | 144.53 J/mol · K | 123.17 J/mol · K |
| $\Delta H_r$ (Van't Hoff) | 87625.6 J/mol | 74760 J/mol |

Using the improved equilibrium data the rate data obtained for the alumina supported zirconium catalyst was re-fitted and additionally the performance of the alumina support itself was evaluated. This new data is presented in Table 7.

TABLE 7

Arrhenius Parameters

| Catalyst | Activation energy ($E_{act}$ J/mol) | | Pre-exponential factor (A, s$^{-1}$) | |
|---|---|---|---|---|
| | New value | Old value (Example 1) | New value | Old value (Example 1) |
| Alumina supported chromia (Example 2) | 29041.2 | N/A | 356.59 | N/A |

TABLE 7-continued

Arrhenius Parameters

| Catalyst | Activation energy ($E_{act}$ J/mol) | | Pre-exponential factor (A, s$^{-1}$) | |
|---|---|---|---|---|
| | New value | Old value (Example 1) | New value | Old value (Example 1) |
| Alumina supported zirconia (Example 1) | 45684.6 | 55700 | 5770.4 | 46910.6 |
| Alumina support | 63531.4 | N/A | 97929.2 | N/A |

COMPARATIVE EXAMPLE 3

Dehydrofluorination of 245fa to 1234ze (High Na $Cr_2O_3$/Alumina)

A chromia catalyst supported on alumina was prepared by impregnation of alumina (ASM Catalysts LLC) having a sodium content of 2170-2410 ppm with $Cr(H_2O)_6Cl_3$. Thus, 17 ml of DI water was added to 24 g of Chromium (III) Chloride hexahydrate. The mixture was heated to 80° C. in a water bath and then allowed to cool before adding 50.2 g of ASM alumina. The alumina was impregnated overnight but impregnation was not even and all water had been absorbed so an extra 13 ml DI water was added and the catalyst left overnight again. The catalyst was dried at 90° C. under vacuum. The catalyst Chromium III loading, as prepared, was nominally 9.36% wt/wt. The resulting catalyst, denoted TR1816, was calcined in air or calcined in nitrogen.

The air- and nitrogen-calcined catalysts were pre-activated as described in Example 2 and 245fa (2.5-60 ml/min) was then fed to reactor. Conversion and yields were determined as a function of temperature and contact time and shown in Tables 8 and 9 below.

TABLE 8

Temperature scan TR1816 (air calcined)

| T (° C.) | Mean CT (s) | 245fa bara | 1234ze bara | HF bara | 245fa in ml/min | 1243zeE mol % | 1243zeZ mol % | 245fa mol % | 245fa ml/min | 1234ze ml/min | HF ml/min | Sum ml/min | Mean flow ml/min |
|---|---|---|---|---|---|---|---|---|---|---|---|---|---|
| 275 | 22.98 | 0.57 | 0.21 | 0.21 | 2.5 | 23.65 | 3.48 | 72.86 | 1.82 | 0.68 | 0.68 | 3.18 | 2.84 |
| 275 | 11.28 | 0.52 | 0.24 | 0.24 | 5 | 27.42 | 4.03 | 68.55 | 3.43 | 1.57 | 1.57 | 6.57 | 5.79 |
| 275 | 5.57 | 0.49 | 0.26 | 0.26 | 10 | 29.86 | 4.46 | 65.67 | 6.57 | 3.43 | 3.43 | 13.43 | 11.72 |
| 275 | 2.79 | 0.50 | 0.25 | 0.25 | 20 | 29.13 | 4.43 | 66.43 | 13.29 | 6.71 | 6.71 | 26.71 | 23.36 |
| 275 | 1.89 | 0.53 | 0.24 | 0.24 | 30 | 26.57 | 4.19 | 69.24 | 20.77 | 9.23 | 9.23 | 39.23 | 34.61 |
| 275 | 0.98 | 0.63 | 0.19 | 0.19 | 60 | 19.86 | 3.18 | 76.96 | 46.18 | 13.82 | 13.82 | 73.82 | 66.91 |
| 300 | 20.61 | 0.41 | 0.30 | 0.30 | 2.5 | 36.41 | 5.83 | 57.77 | 1.44 | 1.06 | 1.06 | 3.56 | 3.03 |
| 300 | 10.14 | 0.37 | 0.32 | 0.32 | 5 | 39.77 | 6.36 | 53.87 | 2.69 | 2.31 | 2.31 | 7.31 | 6.15 |
| 300 | 5.03 | 0.35 | 0.32 | 0.32 | 10 | 41.28 | 6.75 | 51.97 | 5.20 | 4.80 | 4.80 | 14.80 | 12.40 |
| 300 | 2.54 | 0.38 | 0.31 | 0.31 | 20 | 38.86 | 6.37 | 54.77 | 10.95 | 9.05 | 9.05 | 29.05 | 24.52 |
| 300 | 1.74 | 0.44 | 0.28 | 0.28 | 30 | 33.54 | 5.6 | 60.86 | 18.26 | 11.74 | 11.74 | 41.74 | 35.87 |
| 300 | 0.91 | 0.56 | 0.22 | 0.22 | 60 | 24.12 | 4.16 | 71.72 | 43.03 | 16.97 | 16.97 | 76.97 | 68.48 |
| 325 | 19.20 | 0.34 | 0.33 | 0.33 | 2.5 | 42.22 | 6.93 | 50.85 | 1.27 | 1.23 | 1.23 | 3.73 | 3.11 |
| 325 | 9.38 | 0.29 | 0.36 | 0.36 | 5 | 47.24 | 7.85 | 44.91 | 2.25 | 2.75 | 2.75 | 7.75 | 6.38 |
| 325 | 4.58 | 0.24 | 0.38 | 0.38 | 10 | 52.14 | 8.96 | 38.91 | 3.89 | 6.11 | 6.11 | 16.11 | 13.05 |
| 325 | 2.29 | 0.24 | 0.38 | 0.38 | 20 | 52.49 | 9.05 | 38.46 | 7.69 | 12.31 | 12.31 | 32.31 | 26.15 |
| 325 | 1.56 | 0.28 | 0.36 | 0.36 | 30 | 47.87 | 8.44 | 43.69 | 13.11 | 16.89 | 16.89 | 46.89 | 38.45 |
| 325 | 0.82 | 0.41 | 0.30 | 0.30 | 60 | 35.6 | 6.5 | 57.89 | 34.73 | 25.27 | 25.27 | 85.27 | 72.63 |
| 350 | 17.43 | 0.22 | 0.39 | 0.39 | 2.5 | 53.97 | 9.42 | 36.61 | 0.92 | 1.58 | 1.58 | 4.08 | 3.29 |
| 350 | 8.53 | 0.18 | 0.41 | 0.41 | 5 | 58.63 | 10.4 | 30.96 | 1.55 | 3.45 | 3.45 | 8.45 | 6.73 |
| 350 | 4.23 | 0.17 | 0.42 | 0.42 | 10 | 60.82 | 10.75 | 28.43 | 2.84 | 7.16 | 7.16 | 17.16 | 13.58 |
| 350 | 2.12 | 0.18 | 0.41 | 0.41 | 20 | 59.23 | 10.95 | 29.82 | 5.96 | 14.04 | 14.04 | 34.04 | 27.02 |
| 350 | 1.46 | 0.23 | 0.38 | 0.38 | 30 | 52.5 | 9.84 | 37.66 | 11.30 | 18.70 | 18.70 | 48.70 | 39.35 |
| 350 | 0.78 | 0.38 | 0.31 | 0.31 | 60 | 37.47 | 7.32 | 55.21 | 33.13 | 26.87 | 26.87 | 86.87 | 73.44 |
| 375 | 16.46 | 0.19 | 0.41 | 0.41 | 2.5 | 57.65 | 10.61 | 31.74 | 0.79 | 1.71 | 1.71 | 4.21 | 3.35 |
| 375 | 7.90 | 0.12 | 0.44 | 0.44 | 5 | 66.76 | 12.54 | 20.7 | 1.04 | 3.97 | 3.97 | 8.97 | 6.98 |
| 375 | 3.95 | 0.11 | 0.44 | 0.44 | 10 | 66.71 | 13.06 | 20.23 | 2.02 | 7.98 | 7.98 | 17.98 | 13.99 |

TABLE 8-continued

Temperature scan TR1816 (air calcined)

| T (° C.) | Mean CT (s) | 245fa bara | 1234ze bara | HF bara | 245fa in ml/min | 1243zeE mol % | 1243zeZ mol % | 245fa mol % | 245fa ml/min | 1234ze ml/min | HF ml/min | Sum ml/min | Mean flow ml/min |
|---|---|---|---|---|---|---|---|---|---|---|---|---|---|
| 375 | 1.97 | 0.11 | 0.44 | 0.44 | 20 | 65.39 | 14.14 | 20.47 | 4.09 | 15.91 | 15.91 | 35.91 | 27.95 |
| 375 | 1.38 | 0.20 | 0.40 | 0.40 | 30 | 54.36 | 12.04 | 33.59 | 10.08 | 19.92 | 19.92 | 49.92 | 39.96 |
| 375 | 0.75 | 0.36 | 0.32 | 0.32 | 60 | 37.86 | 8.77 | 53.37 | 32.02 | 27.98 | 27.98 | 87.98 | 73.99 |

TABLE 9

Temperature scan TR1816 (nitrogen calcined)

| T (° C.) | Mean CT (s) | 245fa bara | 1234ze bara | HE bara | 245fa in ml/min | 1243zeE mol % | 1243zeZ mol % | 245fa mol % | 245fa ml/min | 1234ze ml/min | HF ml/min | Sum ml/min | Mean flow ml/min |
|---|---|---|---|---|---|---|---|---|---|---|---|---|---|
| 275 | 22.43 | 0.51 | 0.25 | 0.25 | 2.5 | 28.03 | 4.68 | 67.29 | 1.68 | 0.82 | 0.82 | 3.32 | 2.91 |
| 275 | 11.37 | 0.54 | 0.23 | 0.23 | 5 | 25.05 | 4.53 | 70.42 | 3.52 | 1.48 | 1.48 | 6.48 | 5.74 |
| 275 | 5.91 | 0.65 | 0.17 | 0.17 | 10 | 17.75 | 3.20 | 79.06 | 7.91 | 2.09 | 2.09 | 12.09 | 11.05 |
| 275 | 3.08 | 0.79 | 0.10 | 0.10 | 20 | 9.74 | 1.84 | 88.42 | 17.68 | 2.32 | 2.32 | 22.32 | 21.16 |
| 275 | 2.08 | 0.84 | 0.08 | 0.08 | 30 | 7.47 | 1.33 | 91.20 | 27.36 | 2.64 | 2.64 | 32.64 | 31.32 |
| 275 | 1.07 | 0.93 | 0.03 | 0.03 | 60 | 2.71 | 0.66 | 96.63 | 57.98 | 2.02 | 2.02 | 62.02 | 61.01 |
| 300 | 20.19 | 0.36 | 0.32 | 0.32 | 2.5 | 40.11 | 7.21 | 52.69 | 1.32 | 1.18 | 1.18 | 3.68 | 3.09 |
| 300 | 10.26 | 0.40 | 0.30 | 0.30 | 5 | 36.51 | 6.73 | 56.76 | 2.84 | 2.16 | 2.16 | 7.16 | 6.08 |
| 300 | 5.34 | 0.50 | 0.25 | 0.25 | 10 | 28.19 | 5.37 | 66.43 | 6.64 | 3.36 | 3.36 | 13.36 | 11.68 |
| 300 | 2.79 | 0.61 | 0.19 | 0.19 | 20 | 20.07 | 3.94 | 75.99 | 15.20 | 4.80 | 4.80 | 24.80 | 22.40 |
| 300 | 1.91 | 0.70 | 0.15 | 0.15 | 30 | 14.52 | 2.93 | 82.55 | 24.77 | 5.24 | 5.24 | 35.24 | 32.62 |
| 300 | 0.99 | 0.81 | 0.10 | 0.10 | 60 | 8.82 | 1.87 | 89.31 | 53.59 | 6.41 | 6.41 | 66.41 | 63.21 |
| 325 | 18.13 | 0.22 | 0.39 | 0.39 | 2.5 | 54.21 | 9.62 | 36.18 | 0.90 | 1.60 | 1.60 | 4.10 | 3.30 |
| 325 | 9.15 | 0.24 | 0.38 | 0.38 | 5 | 51.73 | 9.64 | 38.63 | 1.93 | 3.07 | 3.07 | 8.07 | 6.53 |
| 325 | 4.76 | 0.32 | 0.34 | 0.34 | 10 | 43.11 | 8.39 | 48.49 | 4.85 | 5.15 | 5.15 | 15.15 | 12.58 |
| 325 | 2.51 | 0.45 | 0.28 | 0.28 | 20 | 31.87 | 6.41 | 61.71 | 12.34 | 7.66 | 7.66 | 27.66 | 23.83 |
| 325 | 1.74 | 0.54 | 0.23 | 0.23 | 30 | 24.6 | 5.09 | 70.31 | 21.09 | 8.91 | 8.91 | 38.91 | 34.45 |
| 325 | 0.91 | 0.68 | 0.16 | 0.16 | 60 | 15.42 | 3.34 | 81.25 | 48.75 | 11.25 | 11.25 | 71.25 | 65.63 |
| 350 | 16.70 | 0.14 | 0.43 | 0.43 | 2.5 | 63.39 | 11.63 | 24.99 | 0.62 | 1.88 | 1.88 | 4.38 | 3.44 |
| 350 | 8.37 | 0.15 | 0.43 | 0.43 | 5 | 62.56 | 11.81 | 25.62 | 1.28 | 3.72 | 3.72 | 8.72 | 6.86 |
| 350 | 4.33 | 0.21 | 0.39 | 0.39 | 10 | 54.3 | 10.89 | 34.81 | 3.48 | 6.52 | 6.52 | 16.52 | 13.26 |
| 350 | 2.31 | 0.34 | 0.33 | 0.33 | 20 | 40.42 | 8.49 | 51.09 | 10.22 | 9.78 | 9.78 | 29.78 | 24.89 |
| 350 | 1.60 | 0.44 | 0.28 | 0.28 | 30 | 31.87 | 6.83 | 61.3 | 18.39 | 11.61 | 11.61 | 41.61 | 35.81 |
| 350 | 0.86 | 0.62 | 0.19 | 0.19 | 60 | 19.18 | 4.51 | 76.31 | 45.79 | 14.21 | 14.21 | 74.21 | 67.11 |
| 375 | 15.63 | 0.10 | 0.45 | 0.45 | 2.5 | 69.72 | 12.8 | 17.48 | 0.44 | 2.06 | 2.06 | 4.56 | 3.53 |
| 375 | 7.82 | 0.10 | 0.45 | 0.45 | 5 | 68.72 | 13.59 | 17.69 | 0.88 | 4.12 | 4.12 | 9.12 | 7.06 |
| 375 | 3.99 | 0.13 | 0.43 | 0.43 | 10 | 63.01 | 13.42 | 23.58 | 2.36 | 7.64 | 7.64 | 17.64 | 13.82 |
| 375 | 2.11 | 0.24 | 0.38 | 0.38 | 20 | 49.73 | 11.3 | 38.97 | 7.79 | 12.21 | 12.21 | 32.21 | 26.10 |
| 375 | 1.47 | 0.33 | 0.33 | 0.33 | 30 | 40.56 | 9.56 | 49.88 | 14.96 | 15.04 | 15.04 | 45.04 | 37.52 |
| 375 | 0.79 | 0.51 | 0.25 | 0.25 | 60 | 26.21 | 6.26 | 67.53 | 40.52 | 19.48 | 19.48 | 79.48 | 69.74 |

The activation energies (kJ/mol) were calculated as described an Example 2 and were found as follows: TR1816 (air-calcined)=36.6 and TR1816 (nitrogen-calcined)=65.1. Comparison of the activation energies of the alumina-supported chromia catalysts in Examples 2 and 3 shows that the low sodium alumina-supported chromia catalyst in Example 2 is significantly more active for the dehydrohalogenation of 245fa.

EXAMPLE 4

Dehydrofluorination of 245fa to 1234ze (High Na ZrO$_2$/Alumina) and Coking Experiments A further zirconia catalyst supported on alumina (denoted TR1817) was prepared having a nominal catalyst Zr loading of 7.5% wt/wt (the actual Zr loading of the catalyst was measured and found to be 1.68% wt/wt). The alumina used was obtained from ASM Catalysts LLC and had a sodium content of 2170-2410 ppm. Using the same catalyst testing conditions as described above for Examples 2 and 3, this catalyst was measured to have an activation energy of 51.1 kJ/mol for the dehydrofluorination of 245fa to 1234ze. This is in good agreement with the zirconia catalyst supported on alumina obtained from a different source described in Example 1.

The ASM alumina-supported zirconia catalyst was compared to the low sodium alumina-supported chromia catalyst of Example 2 in the following coking experiments.

Each catalyst was pre-treated as described in Example 2. 20 ml/min of neat 245fa was then fed over each catalyst (in separate 0.5"×30 cm reactors). The temperature was increased until c.a. 40% conversion was achieved. These conditions were then maintained with temperature being adjusted as required so as to maintain c.a. 40% conversion. The experiments were stopped when this target could no longer be met or the when the temperature had been increased by c.a. 40° C. The relative performance of the two catalysts is shown in FIG. 7. TR1787 was significantly superior to TR1817, achieving the required conversion at just 270° C. and being able to maintain it for c.a. 300 hours.

Temperature programmed oxidation (TPO) profiles were generated for each catalyst using a thermogravimetric analytical (TGA) method. The TGA method for coke determination on spent catalyst samples was as follows:

Basic instrument set up: Instrument purge set to 25 ml/min nitrogen. 30 µl platinum pan containing c.a. 30-100 mg sample either ground or as whole pellet.

1) Sample introduced at 30° C. and furnace purged with nitrogen at 200 ml/min for 5 minutes
2) Purge flow reduced to 100 ml/min for 1 minute
3) Sample heated to 550° C. at 20° C./min under nitrogen at 100 ml/min
4) Purge flow reduced to 50 ml/min and sample held at 550° C. for 15 minutes
5) Sample cooled from 550 to 200° C. at 30° C./min under nitrogen at 25 ml/min
6) Sample stabilised at 200° C. and 25 ml/min nitrogen for 5 minutes
7) Gas flow switched to air at 10 ml/min and system stabilised for 5 minutes
8) Sample temperature ramped to 550° C. at 15° C./min under air at 10 ml/min
9) Dwell 550° C. for 18 minutes under air at 10 ml/min These profiles showed that the coke present on TR1787 was much more easily removed than that on TR1817.

EXAMPLES 5 TO 7

Dehydrofluorination of 245fa to 1234ze (Low and High Na ZrO$_2$/Alumina)

Two zirconia catalysts supported on alumina with low sodium content according to the invention were prepared and compared for their activity in catalysing the dehydrofluorination of 245fa to 1234ze with the zirconia catalysts supported on alumina with high sodium content of Comparative Example 1, Example 4 and a further Comparative Example 7.

All of the catalysts tested zirconia catalysts had measured Zr loadings of between 1 to 3% wt/wt. The catalyst of Example 5 was prepared by adding 4.9 g ZrOCl$_2$.8H$_2$O to 218 g ethanol, and heating to 60° C. to enable the salt to dissolve. 50 g of alumina was added and left to impregnate overnight. The resulting mixture was rotary evaporated at 80° C. to remove the ethanol. The catalyst was then dried in a vacuum oven at 150° C. overnight.

The catalyst of Example 6 was prepared by adding 20 g ZrOCl$_2$.8H$_2$O to 20 ml de-ionised water, and heating to 60° C. to enable the salt to dissolve. 50 g of alumina was added and left to impregnate overnight. The resulting mixture was rotary evaporated at 80° C. to remove the water. The catalyst was then dried in a vacuum oven at 80° C. overnight.

The catalyst of Comparative Example 7 was prepared by adding 20 g ZrOCl$_2$.8H$_2$O to 20 ml de-ionised water, and heating to 60° C. to enable the salt to dissolve. 50 g of alumina was added and left to impregnate overnight. The resulting mixture was rotary evaporated at 80° C. to remove the water. The catalyst was then dried in a vacuum oven at 80° C. overnight.

Prior to the dehydrofluorination experiments, each catalyst was dried at 200° C. with 60 mls/min nitrogen overnight. HF at 30 mls/min diluted with 60 mls/min nitrogen was passed over the catalyst at 300° C. for one hour. The nitrogen was switched off and HF at 30 mls/min was passed at 360° C. for one hour. A nitrogen purge overnight was then carried out to remove traces of HF.

245fa was passed over the catalysts at flow rates of 2.5, 5, 10, 20, 30 and 60 ml/min at the temperatures indicated in Table 10 below. The results of the dehydrofluorination experiments, and the associated kinetic and thermodynamic parameters as determined in accordance with Example 2, are summarised below.

TABLE 10

Summary results for conversion of 245fa to 1234ze over alumina-supported zirconium catalysts

| | Example | | | | |
|---|---|---|---|---|---|
| | 1 (comparative) | 4 (comparative) | 5 | 6 | 7 (Comparative) |
| Preparative Solvent | EtOH | EtOH | EtOH | Water | Water |
| Na (ppm) | 2340 | 2170 | 76 | 353 | 2170 |
| Temperature (° C.) | Net Rate Constant (s$^{-1}$) | | | | |
| 275 | 0.26 | 0.11 | 0.22 | 0.37 | 0.15 |
| 300 | 0.36 | 0.20 | 0.38 | 0.80 | 0.28 |
| 325 | 0.62 | 0.29 | 0.70 | 0.90 | 0.45 |
| 350 | 0.95 | 0.50 | 1.00 | 1.10 | 0.75 |
| 375 | 1.10 | 0.60 | 1.50 | 1.70 | 1.10 |
| Arrhenius Parameters | | | | | |
| Activation energy (kj/mol) | 45.68 | 51.14 | 56.95 | 40.03 | 58.83 |
| LnA | 8.66 | 9.07 | 11.008 | 7.94 | 11.04 |
| Temperature Required To Achieve Net Rate Constant | | | | | |
| 1.0 s$^{-1}$ | 361 | 405 | 349 | 333 | 368 |
| 1.5 s$^{-1}$ | 393 | 437 | 373 | 366 | 392 |
| 2.0 s$^{-1}$ | 417 | 461 | 391 | 391 | 411 |

Inspection of the temperatures required to achieve the net rate constants shown demonstrates that the low sodium alumina-supported ZrO$_2$ catalyst of the invention prepared in ethanol (See Example 5) compares favourably with the corresponding high sodium alumina-supported ZrO$_2$ catalysts (see Examples 1 and 4). Likewise, the low sodium alumina-supported ZrO$_2$ catalyst of the invention prepared in water (see Example 6) compares favourably with the corresponding high sodium alumina-supported ZrO$_2$ catalyst (see Example 7).

EXAMPLES 8 AND 9

Dehydrofluorination of 245fa to 1234ze (Low and High Na Cr$_2$O$_3$/Alumina)

With reference to Example 2 and Comparative Example 3, two further chromia catalysts supported on alumina were prepared_ and compared for their activity in catalysing the dehydrofluorination of 245fa to 1234ze.

The catalyst of Comparative Example 8 was prepared by dissolving 10 g CrO$_3$ in 20 g de-ionised water. 50 g of alumina was added and left to impregnate overnight. The resulting mixture was rotary evaporated at 80° C. to remove the water. The catalyst was then dried in a vacuum oven at 50° C. for 2 days.

The catalyst of Example 9 was prepared by dissolving 10 g CrO$_3$ in 20 g de-ionised water. 50 g of alumina was added and left to impregnate overnight. The resulting mixture was rotary evaporated at 80° C. to remove the water. The catalyst was then dried in a vacuum oven at 50° C. for 2 days.

Prior to the dehydrofluorination experiments, each catalyst was dried at 200° C. with 60 mls/min nitrogen overnight, followed by one hour at 360° C. with 60 mls/min nitrogen to calcine the catalyst. HF at 30 mls/min diluted with 60 mls/min nitrogen was passed over the catalyst at 300° C. for one hour. The nitrogen was switched off and HF at 30 mls/min was passed at 360° C. for one hour. A nitrogen purge overnight was then carried out to remove traces of HF.

245fa was passed over the catalysts at flow rates of 2.5, 5, 10, 20, 30 and 60 ml/min at the temperatures indicated in Table 11 below. The results of the dehydrofluorination experiments, and the associated kinetic and thermodynamic parameters as determined in accordance with Example 2, are summarised below.

TABLE 11

Summary results for conversion of 245fa to 1234ze over alumina-supported chromium oxide catalysts

| | Example | | |
|---|---|---|---|
| | 2 | 8 (comparative) | 9 |
| Preparative Solvent | Water | Water | Water |
| $Cr_2O_3$ (% wt) | 21.8 | 10.55 | 12.22 |
| Na (ppm) | 111 | 2170 | 353 |
| Temperature (° C.) | Net Rate Constant ($s^{-1}$) | | |
| 275 | 0.60 | 0.25 | 0.475 |
| 300 | 0.78 | 0.30 | 0.80 |
| 325 | 1.10 | 0.55 | 1.05 |
| 350 | 1.35 | 0.73 | 1.30 |
| 375 | 1.55 | 0.90 | 2.00 |
| Arrhenius Parameters | | | |
| Activation energy (kj/mol) | 29.04 | 40.82 | 39.76 |
| LnA | 5.88 | 7.52 | 8.03 |
| Temperature required to achieve Net Rate constant= | | | |
| 1.0 $s^{-1}$ | 321 | 380 | 323 |
| 1.5 $s^{-1}$ | 365 | 417 | 354 |
| 2.0 $s^{-1}$ | 400 | 446 | 379 |

Again, inspection of the temperatures required to achieve the net rate constants shown demonstrates that the low sodium alumina-supported chromia catalysts of the invention (Examples 2 and 9) compare favourably with the corresponding high sodium alumina-supported chromia catalyst (Example 8).

EXAMPLES 10 AND 11

Dehydrofluorination of $CF_3CF_2CH_3$ (245cb) to $CF_3CF=CH_2$ (1234yf) Low and High Na $Cr_2O_3$/Alumina)

The same chromia catalysts supported on alumina used in Examples 8 and 9 were compared for their activity in catalysing the dehydrofluorination of 245cb to 1234yf.

Prior to the dehydrofluorination experiments, each catalyst was dried at 200° C. with 60 mls/min nitrogen overnight, followed by one hour at 360° C. with 60 mls/min nitrogen to calcine the catalyst. HF at 30 mls/min diluted with 60 mls/min nitrogen was passed over the catalyst at 300° C. for one hour. The nitrogen was switched off and HF at 30 mls/min was passed at 360° C. for one hour. A nitrogen purge overnight was then carried out to remove traces of HF.

245cb was passed over the catalysts at 2.5 ml/min at 375° C. The results of the dehydrofluorination experiments are summarised below.

TABLE 12

Summary results for dehydrofluorination of 245cb to 1234yf

| | Example | |
|---|---|---|
| | 10 (comparative) | 11 |
| Preparative Solvent | Water | Water |
| $Cr_2O_3$ (% wt) | 10.55 | 12.22 |
| Na (ppm) | 2170 | 353 |
| 245cb Conversion at 375° C. (mol %) | 24.0 | 38.9 |

Use of the low sodium chromia catalyst supported on alumina (Example 11) resulted in higher conversion of 245cb than the high sodium chromia catalyst supported on alumina (Example 10) at the same reaction temperature.

EXAMPLES 12 AND 13

Dehydrofluorination of $CF_3CHFCH_2F$ (245eb) to $CF_3CF=CH_2$ (1234yf) (Low and High Na $Cr_2O_3$/Alumina)

The same chromia catalysts supported on alumina used in Examples 8 to 11 were compared for their activity in catalysing the dehydrofluorination of 245eb to 1234yf. The catalysts were both dried at 200° C. with 60 mls/min nitrogen for an hour, followed by one hour at 360° C. with 60 mls/min nitrogen to calcine the catalyst. HF at 30 mls/min diluted with 60 mls/min nitrogen was passed over the catalyst at 300° C. for one hour. The nitrogen was switched off and HF at 30 mls/min was passed at 360° C. for one hour.

245eb was passed over the catalysts at 300° C. with flow rates as shown in Table 13 below. The results of the dehydrofluorination experiments are summarised below.

TABLE 13

Summary results for dehydrofluorination of 245eb to 1234yf

| | Example | | |
|---|---|---|---|
| | 12 (comparative) | 13a | 13b |
| Preparative Solvent | Water | Water | Water |
| $Cr_2O_3$ (% wt) | 10.55 | 12.22 | 12.22 |
| Na (ppm) | 2170 | 353 | 353 |
| 245eb flow rate (ml/min) | 5 | 2.5 | 5 |
| 245eb Conversion (area %) | 34.75 | 95.2 | 74.96 |

Use of the low sodium chromia catalyst supported on alumina (Examples 13a-b) resulted in higher conversion of 245eb than the high sodium chromia catalyst supported on alumina (Example 12) at the same reaction temperature.

EXAMPLES 14 COMPARATIVE AND 15

Dehydrofluorination of $CF_3CH_2CH_2F$ (254fb) to $CF_3CH=CH_2$ (1243zf) (Low and High Na $Cr_2O_3$/Alumina)

The same chromia catalysts supported on alumina used in Examples 8 to 13 were compared for their activity in catalysing the dehydrofluorination of 254fb to 1243zf.

Prior to the dehydrofluorination experiments, each catalyst was dried at 200° C. with 60 mls/min nitrogen overnight, followed by one hour at 360° C. with 60 mls/min nitrogen to calcine the catalyst. HF at 30 mls/min diluted with 60 mls/min nitrogen was passed over the catalyst at 300° C. for one hour. The nitrogen was switched off and HF at 30 mls/min was passed at 360° C. for one hour. A nitrogen purge overnight was then carried out to remove traces of HF.

245cb was passed over the catalysts at 5, 10 and 20 ml/min at 225° C. or 275° C. The results of the dehydrofluorination experiments are summarised below.

TABLE 14

Summary results for dehydrofluorination of 254fb to 1243zf

| | Example | | | | |
|---|---|---|---|---|---|
| | 14a (comp) | 14b (comp) | 14c (comp) | 15a | 15b |
| Preparative Solvent | Water | Water | Water | Water | Water |
| $Cr_2O_3$ (% wt) | 10.55 | 10.55 | 10.55 | 12.22 | 12.22 |
| Na (ppm) | 2170 | 2170 | 2170 | 353 | 353 |
| 254fb flow rate (ml/min) | 5 | 10 | 20 | 5 | 20 |
| Temperature | 275 | 225 | 225 | 275 | 225 |
| Mol % 1243zf in reaction off-gas | 91.74 | 30.07 | 10.36 | 98.28 | 87.13 |
| Mol % 254fb in reaction off-gas | 3.85 | 68.88 | 87.75 | 0.14 | 10.34 |

The conversion of 254fb to 1243zf was greater, at the same 254fb flow rate and reaction temperature, with the use of the low sodium chromia catalyst supported on alumina (Examples 15a-b) compared to the high sodium chromia catalyst supported on alumina (Examples 14a-c).

The above examples demonstrate that alumina-supported metal oxide catalysts with a low sodium content are surprisingly active and robust for dehydrohalogenation of $C_{3-7}$ hydro(halo)alkanes when compared to corresponding catalysts with higher sodium content. This allows operating temperatures to be minimised, and by doing so, fouling is minimised and selectivity maximised. Furthermore, certain of the low sodium alumina-supported metal oxide catalysts have been shown to be easy to regenerate. The combination of high catalyst activity and selectivity for the preparation of $C_{3-7}$ (hydro)fluoropropenes by dehydrohalogenation, in addition to ease of catalyst regeneration, is completely unexpected.

The invention is defined by the following claims.

The invention claimed is:

1. A process for preparing a $C_{3-7}$ (hydro)fluoroalkene comprising dehydrohalogenating a $C_{3-7}$ hydro(halo)fluoroalkane in the presence of a catalyst consisting of a metal oxide supported on alumina, wherein the catalyst has a sodium content of less than about 800 ppm, wherein the metal of the metal oxide is a transition metal selected from the group consisting of Cr, Nb, Ta, V, Mo, or Co and optionally wherein the catalyst further contains at least one additional metal selected from the group consisting of Zn, Cr, In, Co and mixtures thereof.

2. A process according to claim 1, wherein the catalyst has a sodium content of less than about 500 ppm.

3. A process according to claim 1, wherein die catalyst comprises said metal oxide and at least 60% by weight of the alumina support based on the total weight of the catalyst.

4. A process according to claim 1, wherein the metal of the metal oxide is Cr.

5. A process according to claim 1, wherein the catalyst contains up to about 40% by weight of the metal oxide based on the total weight of the catalyst.

6. A process according to claim 1, wherein the catalyst comprises up to about 20% by weight of the at least one additional metal or a compound of the additional metal, based on the total weight of the catalyst.

7. A process according to claim 1 comprising dehydrohalogenating the $C_{3-7}$ hydro(halo)fluoroalkane in the absence of added hydrogen fluoride (HF).

8. A process according to claim 1 carried out at a temperature of from out 50 to about 400° C. and a pressure of up to about 30 bara.

9. A process according to claim 1 for preparing (hydro)fluoropropene comprising dehydrohalogenating a hydro(halo)fluoropropane.

10. A process according to claim 9 wherein the (hydro)fluoropropene produced is selected from the group consisting of trifluoropropenes, tetrafluoropropenes and pentafluoropropenes.

11. A process according claim 9 for preparing 1,3,3,3-tetrafluoropropene (HFO-1234ze) comprising dehydrofluorinating 1,1,1,3,3-pentafluoropropane (HFC-245fa).

12. process according to claim 9 for preparing 2,3,3,3-tetrafluoropropene (HFO-1234yf) comprising at least one of dehydrolluorinating 1,1,1,2,2-pentaftuoropropane (HFC-245cb) arid 1,1,1,2,3-pentafluoropropane (HFC-245eb).

13. A process according to claim 9 for preparing 1,2,3,3,3-pentafluoropropene (HFO-1225ye) comprising dehydrofluorinating 1,1,1,2,3,3-hexaftuoropropane (HFC-236ea).

14. A process according to claim 1, wherein the catalyst has a sodium content of less than about 150 ppm.

15. A process according to claim 1, wherein the catalyst contains said metal oxide and at least 70% A by weight of the alumina support based on the total weight of the catalyst.

16. A process according to claim 1, wherein the catalyst contains to about 30% by weight of the metal oxide based on the total weight of the catalyst.

17. A process according to claim 1, wherein at least one additional compound of a metal is present as a compound.

18. A process according to claim 17, wherein the at least one additional compound of metal is selected from the group consisting of at least one of Zn, Cr, In, Co, arid mixtures thereof.

19. A process according to claim 17, wherein the catalyst contains up to about 20 % by weight of the at least one compound of additional metal based on the total weight of the catalyst.

20. A process according to claim 17, wherein the catalyst contains up to about 10% by weight of the at least one compound of additional metal based on the total weight of the catalyst.

21. A process according to claim 1, wherein the catalyst comprises un to about 10% by weight of the at least one additional metal based on the total weight of the catalyst.

* * * * *

UNITED STATES PATENT AND TRADEMARK OFFICE
CERTIFICATE OF CORRECTION

PATENT NO. : 10,167,242 B2  
APPLICATION NO. : 14/398252  
DATED : January 1, 2019  
INVENTOR(S) : Andrew P. Sharratt, Claire E. McGuinness and Sheryl C. Carolan Page 1 of 1

It is certified that error appears in the above-identified patent and that said Letters Patent is hereby corrected as shown below:

In the Claims

Column 24, Claim 3, Line 1:  
"...wherein die catalyst..." should read --...wherein the catalyst...--

Column 24, Claim 12, Line 29:  
"process according to claim 9..." should read --A process according to claim 9...--

Column 24, Claim 12, Line 31:  
"dehydrolluorinating..." should read --dehydrofluorinating...--

Column 24, Claim 13, Line 35:  
"...hexaftuoropropane..." should read --...hexafluoropropane...--

Column 24, Claim 15, Line 39:  
"...70% A by weight..." should read --...70% by weight...--

Column 24, Claim 21, Line 59:  
"comprises un to about..." should read --comprises up to about--

Signed and Sealed this  
Twenty-first Day of April, 2020

Andrei Iancu  
*Director of the United States Patent and Trademark Office*